US011724127B2

(12) United States Patent
Constantin et al.

(10) Patent No.: US 11,724,127 B2
(45) Date of Patent: Aug. 15, 2023

(54) BEAM SPOT TUNING IN A RADIATION THERAPY SYSTEM

(71) Applicant: VARIAN MEDICAL SYSTEMS, INC., Palo Alto, CA (US)

(72) Inventors: Magdalena Constantin, Los Altos, CA (US); Marcelo Cassese, Menlo Park, CA (US)

(73) Assignee: VARIAN MEDICAL SYSTEMS, INC., Palo Alto, CA (US)

( * ) Notice: Subject to any disclaimer, the term of this patent is extended or adjusted under 35 U.S.C. 154(b) by 134 days.

(21) Appl. No.: 17/216,693

(22) Filed: Mar. 30, 2021

(65) Prior Publication Data
US 2022/0314028 A1 Oct. 6, 2022

(51) Int. Cl.
*A61N 5/10* (2006.01)

(52) U.S. Cl.
CPC ......... *A61N 5/1043* (2013.01); *A61N 5/1031* (2013.01); *A61N 2005/1089* (2013.01)

(58) Field of Classification Search
CPC ...................................................... A61N 5/10
See application file for complete search history.

(56) References Cited

U.S. PATENT DOCUMENTS

| | | | |
|---|---|---|---|
| 2003/0169849 A1 | 9/2003 | Smyth | |
| 2015/0352376 A1* | 12/2015 | Wiggers | A61B 6/06 378/207 |
| 2016/0114190 A1 | 4/2016 | Brown et al. | |
| 2017/0007848 A1* | 1/2017 | Drees | G21K 5/04 |
| 2020/0206539 A1 | 7/2020 | Han et al. | |
| 2022/0314029 A1 | 10/2022 | Constantin | |

OTHER PUBLICATIONS

International Search Report and Written Opinion of the International Searching Authority, International application No. PCT/US2022/022083, dated Jun. 22, 2022.
Balazs J. Nyiri et al., "Two Self-Referencing Methods for the Measurement of Beam Spot Position", Medical Physics, Dec. 2012, vol. 39, No. 12, pp. 7635-7643.
International Search Report and Written Opinion of the International Searching Authority, International application No. PCT/US2022/022082, dated Jun. 22, 2022.

(Continued)

*Primary Examiner* — Eliza W Osenbaugh-Stewart
(74) *Attorney, Agent, or Firm* — Su IP Consulting

(57) ABSTRACT

An example computer-implemented method for tuning a beam spot in a radiation therapy system has been disclosed. The example method includes configuring an electron beam to generate a first beam spot on an electron-beam target of the radiation therapy system, generating, using an imager of the radiation therapy system, a first plurality of projection images of the first beam spot, wherein each of the projection images of the first beam spot is generated with a line of sight blocked between the imager and a different respective portion of the beam spot, based on the first plurality of projection images, determining a value for one or more beam spot quality metrics associated with the first beam spot, and based on the value, determining whether the first beam spot is outside a specified quality range.

20 Claims, 14 Drawing Sheets

(56) References Cited

OTHER PUBLICATIONS

Andrew Jeung et al., "Dual Edge Apparatus and Algorithm for Measurement of X-Ray Beam Spot Parameters", Medical Physics., Oct. 12, 2018, pp. 5080-5093, vol. 45, No. 11.
Andrew Jeung et al., "Dual Edge Apparatus and Algorithm for Measurement of X-Ray Beam Spot Parameters", Med. Phys., Nov. 2018, pp. 5080-5093, No. 45, vol. 11, 2018 American Association of Physicists in Medicine.

* cited by examiner

BEAM SPOT TUNING IN A RADIATION THERAPY SYSTEM

CROSS-REFERENCE TO RELATED APPLICATION

The present application is also related in subject matter to U.S. patent application Ser. No. 17/216,695, filed Mar. 30, 2021, which is incorporated herein by reference.

BACKGROUND

Unless otherwise indicated herein, the approaches described in this section are not prior art to the claims in this application and are not admitted to be prior art by inclusion in this section.

Radiation therapy is a localized treatment for a specific anatomical target (a planning target volume, or PTV), such as a cancerous tumor. Ideally, radiation therapy is performed on the planning target volume that spares the surrounding normal tissue from receiving doses above specified tolerances, thereby minimizing risk of damage to healthy tissue. Prior to the delivery of radiation therapy, an imaging system is typically employed to provide a three-dimensional image of the anatomical target and surrounding area. From such imaging, the size and mass of the anatomical target can be estimated, a planning target volume determined, and an appropriate treatment plan generated using a dedicated treatment planning system (TPS). The TPS has photon- and electron-beam models that accurately represent the beams generated by the radiation therapy delivery system.

Currently, the field of radiation oncology is moving to treating smaller planning target volumes, for example via stereotactic radiosurgery (SRS) and stereotactic radiotherapy (SRT). Stereotactic radiosurgery and stereotactic radiation therapy are advanced forms of radiation therapy that involve delivery of a high radiation dose to a small focused region of a patient's anatomy. Because of the high radiation dose and small target volumes associated with these SRS treatments, high geometric accuracy of the delivered treatment is required. This high geometrical accuracy is required for both the predicted dose distribution provided by the beam model in the TPS and the delivered dose provided by the actual treatment delivery system.

SUMMARY

According to various embodiments, a computer-implemented procedure includes a direct measurement of beam spot size, shape, and intensity distribution in a radiation therapy system using an existing imaging panel of the radiation therapy system, and modification of one or more attributes of a beam spot based on such measurements. Specifically, a sequence of radiation projection images (e.g., X-ray projection images) are acquired with the imaging panel while a treatment beam is generated and a multi-leaf collimator is positioned to block a portion of the beam and rotated about the center axis of the beam. Based on the projection images, a two-dimensional (2D) image of the beam spot is reconstructed, which indicates the area, size, shape, location, and 2D intensity topography of the beam spot. Additionally, by shaping a small radiation field and using the existing imaging panel to measure the radiation field penumbra and output factor of the treatment beam can be determined. The computer-implemented procedure further includes modifying the size, shape, and/or location of the beam spot based on the reconstructed 2D beam spot image, so that the beam spot meets a threshold value for one or more predetermined quality metrics. In some embodiments, the beam spot can be modified by changing an existing value for a parameter of an electron-beam-generating component of the system to a new value. Additional iterations of beam spot measurement and electron-beam modifications can be performed until the beam spot meets such threshold values. Because each iteration can be performed in a few minutes as part of an automated process, the computer-implemented procedure of the embodiments can be employed as part of factory setup, an on-site quality-assurance tool, and/or as a periodic service tool. Thus, penumbra and/or output factor deviations and other issues created by asymmetric beam spots or beams that do not meet the necessary geometrical requirements can be prevented. Further, a radiation target energy density per unit beam area can be confirmed to be within acceptable limits, thereby ensuring reliable target power levels and extended target life for a radiation therapy system.

According to various embodiments, a computer-implemented procedure includes measurement of one or more attributes of a radiation field generated by a beam spot using an existing imaging panel of the radiation therapy system, and modification of one or more attributes of the beam spot based on such radiation field measurements. Attributes of the radiation field are quantified via one or more specific radiation field quality metrics, which can indicate whether a radiation beam originating from the beam spot is outside a specified quality range. Examples of such radiation field quality metrics include one or more of an area coincidence factor, a penumbra asymmetry factor, and a radiation beam output factor.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of the present disclosure will become more fully apparent from the following description and appended claims, taken in conjunction with the accompanying drawings. These drawings depict only several embodiments in accordance with the disclosure and are, therefore, not to be considered limiting of its scope. The disclosure will be described with additional specificity and detail through use of the accompanying drawings.

DETAILED DESCRIPTION

Figure 1:
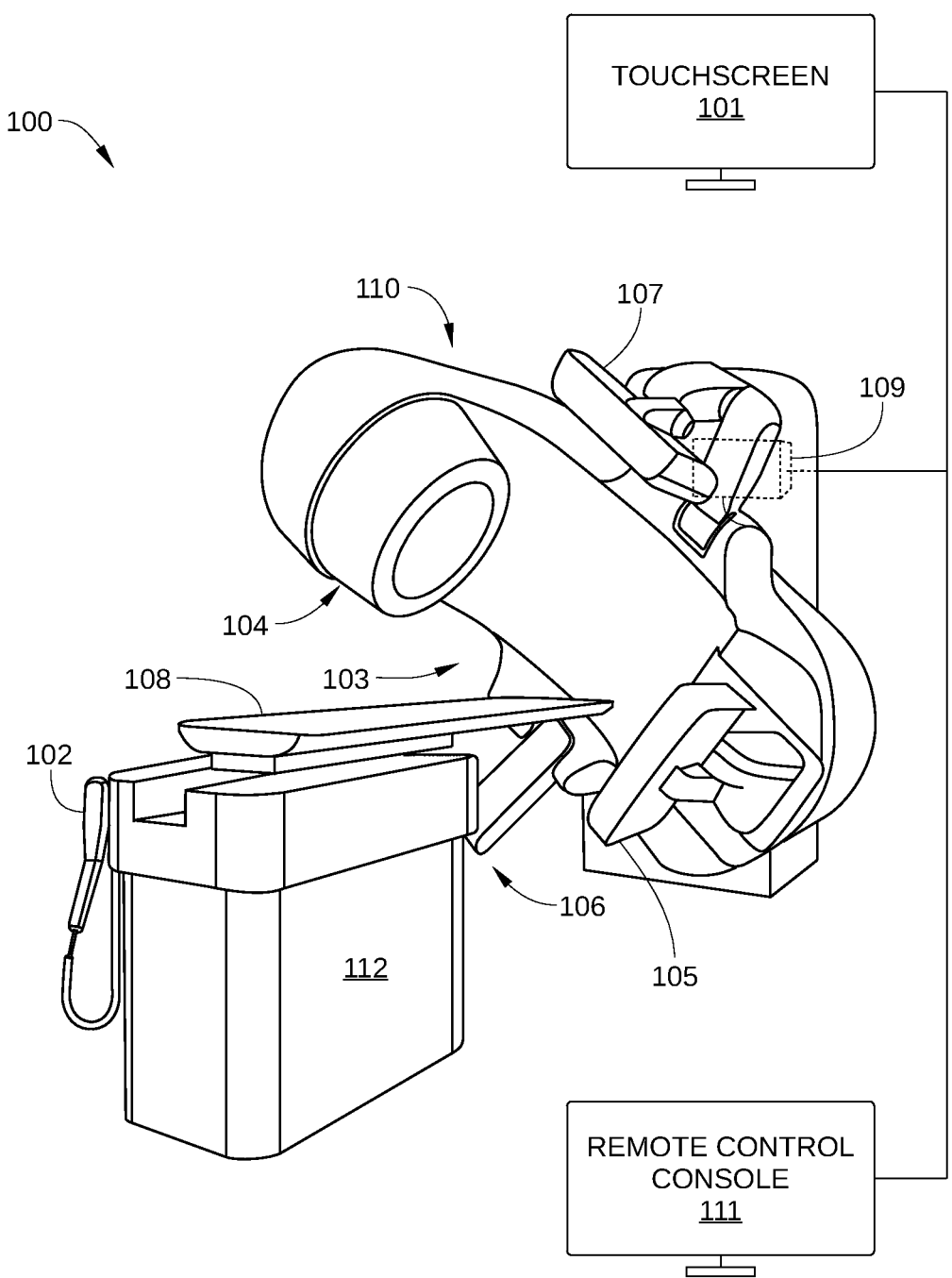
FIG. 1 is a perspective view of a radiation therapy system that can beneficially implement various aspects of the present disclosure.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the disclosure, as generally described herein, and illustrated in the figures, can be arranged, substituted, combined, and designed in a wide variety of different configurations, all of which are explicitly contemplated and make part of this disclosure.

INTRODUCTION

As noted above, for radiation treatments that involve a high radiation dose and/or a small target size, high geometric accuracy of the delivered radiation treatment is required. Many factors can affect the accuracy of a delivered radiation treatment, including the size, shape, and location of the beam spot, which is the area on a radiation target that is struck by an electron beam and generates the treatment radiation beam, such as an X-ray beam or other radiation beam, in linear-accelerator-based radiation therapy systems. For example, to achieve the high spatial accuracy required for certain image-guided radiation therapy (IGRT) treatments, the IGRT imaging isocenter must closely coincide with the treatment beam isocenter, and this isocenter coincidence is influenced by the alignment of the beam spot with the collimator rotation axis. In another example, percentage depth dose distribution and beam profiles of very small diameter (1.5-5 mm) megavoltage (MV) radiosurgical beams have been shown to depend on the diameter of the beam spot. In a further example, controlling and minimizing dose fall-off at the edges of a treatment beam (i.e., the "penumbra") is important for sparing organs at risk in radiation therapy, and the size, shape, and symmetry of the beam spot all directly affect the size and shape of the penumbra. Moreover, the output factor of such small fields, which is also dependent on the beam spot characteristics, has to meet tight specifications. In light of the above, accurate knowledge of the geometry of a beam spot in a radiation therapy system is of high importance, particularly for treatments involving a smaller planning target volume (PTV) and/or a high radiation dose and/or a sharp dose fall-off.

Unfortunately, direct measurement of the beam spot in a radiation therapy system can be difficult to implement. As a result, fitting a planning target volume with a high, uniform dose while limiting the irradiation of neighboring healthy tissues can be difficult to achieve. Conventional techniques for measuring properties of the beam spot of a radiation therapy system are time-consuming to set up and perform, rely on measuring equipment that is external to the radiation therapy system, and/or provide incomplete information about the beam spot. For example, a spot camera positioned between the radiation source of n radiation therapy system and an electronic portal imaging device (EPID) of the radiation therapy system allows only parallel radiation from the radiation source to reach the EPID. As a result, the EPID can generate an image of the beam spot that shows the size, shape, and position of the beam spot. However, a spot camera is a bulky piece of specialized equipment external to the radiation therapy system, requiring precise and time-consuming setup and training to be used. In another example, a probe external to a radiation therapy system can be employed in conjunction with a water tank to traverse the radiation field of the radiation source and generate profiles of radiation intensity across the radiation field. Such profiles can provide relative information about the beam spot and penumbra symmetry. However, this approach also involves the time-consuming setup and manual operation of equipment external to the radiation therapy system, greatly limiting where and how frequently this approach can be employed. Further, the information obtained does not indicate the actual size of the penumbra or the intensity distribution of the beam spot itself.

According to various embodiments, a computer-implemented procedure includes a direct measurement of beam spot size, shape, location, orientation, and intensity distribution in a radiation therapy system, using an existing ("on-board") imaging panel of the radiation therapy system. Based on a sequence of projection images that are acquired with the on-board imaging panel, a two-dimensional (2D) image of the beam spot is reconstructed, which indicates the area, size, shape, location, orientation, and 2D intensity topography of the beam spot, including the radiation penumbra and the output factor of the treatment beam. Radiation penumbra is a parameter describing the dose delivered and the fall-off of dose profiles in the patient, and in some embodiments is given by the difference between the projected distances of the 80% and 20% dose values in a 2-dimensional projection of the dose distribution. For the small fields employed in SRS treatments, penumbra is highly dependent on the radiation beam spot size, shape, and location with respect to the central axis of the collimator system of the radiation therapy system. Additionally, the radiation output factor of the SRS field is dependent on certain beam spot characteristics. Therefore, enforcing predetermined quality metrics on the beam spot ensures that both the penumbra and output factors are tightly controlled and meet tight tolerances mandated by the geometrical accuracy of SRS treatments and small field dosimetry. The beam spot and penumbra of a treatment beam in a radiation therapy system are described in greater detail below in conjunction with FIGS. 3-5.

In some embodiments, the computer-implemented procedure further includes modifying the size, shape, and/or location of the beam spot and/or penumbra based on the reconstructed 2D beam spot image, so that the beam spot meets a threshold value for one or more predetermined beam spot quality metrics. In some embodiments, such beam spot quality metrics include one or more of a beam spot area, a beam spot elongation, a beam spot power per unit area factor, and/or a beam spot center point offset from an ideal center point location.

The herein-described embodiments facilitate tuning of a beam spot to achieve superior beam quality metrics and improve consistency between the attributes of the beam spot and the overall beam tuning of the treatment delivery system and pre-configured beam data that is included in a treatment planning model of a TPS. Pre-configured beam data is a set of beam measurements (e.g., beam profiles, percent depth dose and/or output factors) acquired using a dedicated 3-dimensional water scanning system and radiation detectors. Generally, such pre-configured beam data resides in the TPS that is used for treatment plan creation. As a result, in the embodiments, performance of a radiation beam generated by the beam spot closely matches the performance assumed for the radiation beam in the TPS.

SYSTEM OVERVIEW

FIG. 1 is a perspective view of a radiation therapy system 100 that can beneficially implement various aspects of the present disclosure. Radiation therapy (RT) system 100 is a radiation system may be configured to detect intra-fraction motion in near-real time using X-ray imaging techniques. Thus, in some embodiments, RT system 100 is configured to provide stereotactic radiosurgery and precision radiotherapy for lesions, tumors, and conditions anywhere in the body where radiation treatment is indicated. As such, RT system 100 can include one or more of a linear accelerator (LINAC) 104 that generates an MV treatment beam of high energy X-rays or other radiation, one or more kilovolt (kV) X-ray sources 106, one or more imaging panels 107 (e.g., an X-ray imager), and an MV electronic portal imaging device (EPID) 105. By way of example, RT system 100 is described herein configured with a C-arm gantry 110 capable of infinite rotation via a slip ring connection. In other embodiments, RT system 100 can be configured with a circular gantry mounted on a drive stand, or any other technically feasible configuration that enables radiation therapy and imaging of a PTV.

In some embodiments, RT system 100 is capable of X-ray imaging of a target volume immediately prior to and/or during application of an MV treatment beam, so that an IGRT and/or an intensity-modulated radiation therapy (IMRT) process can be performed using X-ray imaging. For example, in some embodiments, RT system 100 includes kV imaging of a PTV in conjunction with imaging generated by the MV treatment beam. RT system 100 may include one or more touchscreens 101 for patient information verification, couch motion controls 102, a radiation area 103, a base positioning assembly 112, a couch 108 disposed on base positioning assembly 112, and an image acquisition and treatment control computer 109, all of which are disposed within a treatment room. RT system 100 further includes a remote control console 111, which is disposed outside the treatment room and enables treatment delivery and patient monitoring from a remote location. In some embodiments, image acquisition and treatment control computer 109 and/or remote control console 111 is configured to execute a treatment planning system that includes photon-beam, electron-beam, and/or other treatment planning models that accurately represent the beams generated by RT system 100. Such models include pre-configured beam data that assumes specific attributes of the beam spot that generates a treatment beam. Base positioning assembly 112 is configured to precisely position couch 108 with respect to radiation area 103, and motion controls 102 include input devices, such as buttons and/or switches, that enable a user to operate base positioning assembly 112 to automatically and precisely position couch 108 to a predetermined location with respect to radiation area 103. Motion controls 102 also enable a user to manually position couch 108 to a predetermined location.

Figure 2:
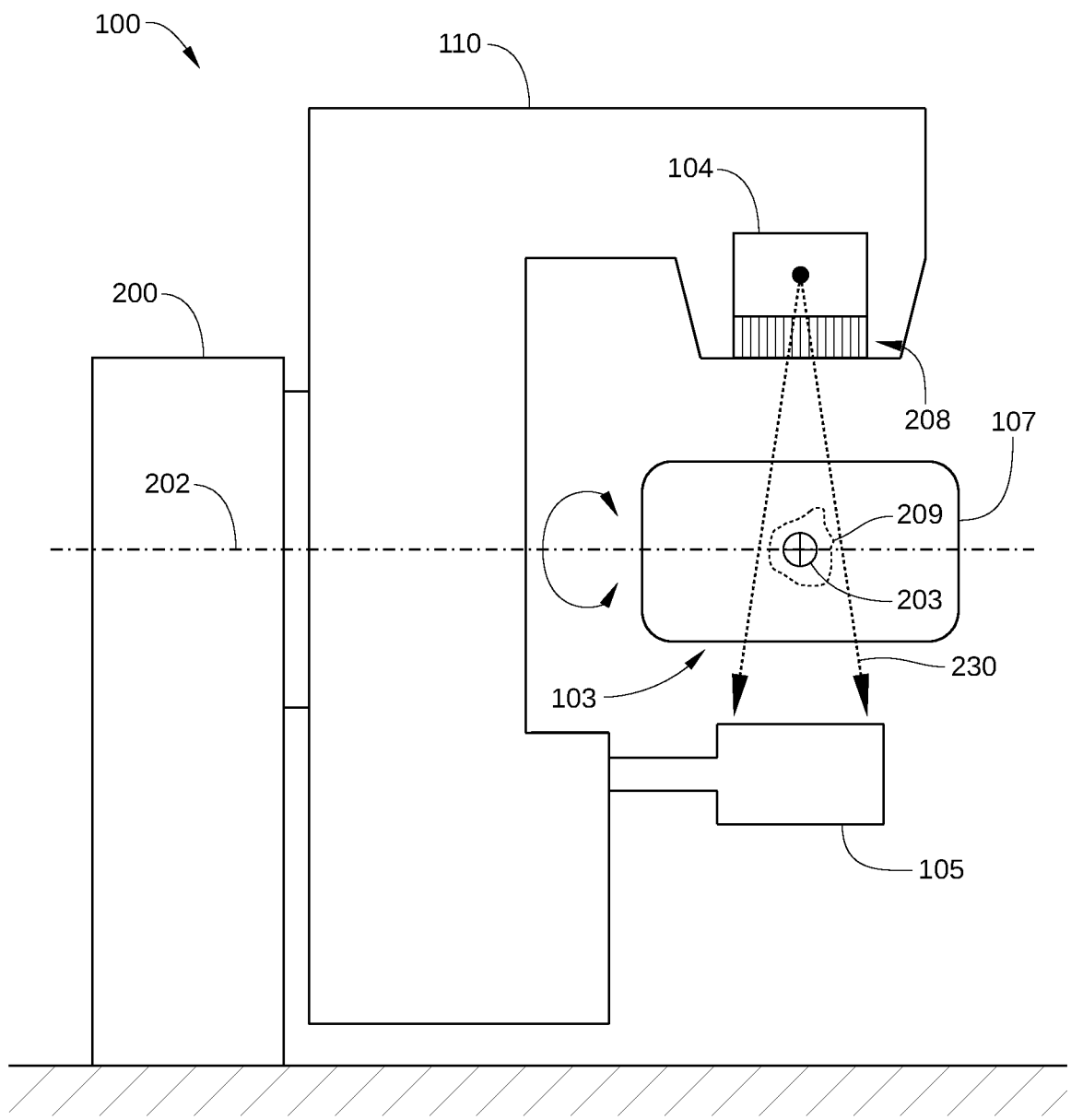
FIG. 2 schematically illustrates a side view of the radiation therapy system of FIG. 1, according to various embodiments.

FIG. 2 schematically illustrates a side view of RT system 100, according to various embodiments. As shown, RT system 100 includes a base stand 200 and C-arm gantry 110. In FIG. 2, base positioning assembly 112, couch 108, and X-ray source 106 are omitted for clarity. Base stand 200 is a fixed support structure for components of RT treatment system 100, including C-arm gantry 110 and a drive system (not shown) for rotatably moving C-arm gantry 110 about a horizontal rotation axis 202. Base stand 200 rests on and/or is fixed to a support surface that is external to RT treatment system 100, such as a floor of an RT treatment facility. C-arm gantry 110 is rotationally coupled to base stand 200 and is a support structure on which various components of RT system 100 are mounted, including LINAC 104, EPID 105, imaging X-ray source 106 (not shown in FIG. 2), and imaging panel 107. During operation of RT treatment system 100, C-arm gantry 110 rotates about radiation area 103 when actuated by the drive system.

Imaging X-ray source 106 is configured to direct a conical beam of X-rays, referred to herein as imaging X-rays (not shown in FIG. 2 for clarity), through an isocenter 203 of RT system 100 to imaging panel 107. Isocenter 203 typically corresponds to the location of a target volume 209 to be treated, such as a PTV. In the embodiment illustrated in FIG. 2, imaging panel 107 is depicted as a planar device, whereas in other embodiments, imaging panel 107 can have a curved configuration. In the embodiment illustrated in FIGS. 1 and 2, RT system 100 includes a single imaging panel and a single corresponding imaging radiation source in addition to EPID 105. In other embodiments, RT system 100 can include two or more imaging panels, each with a corresponding imaging radiation source.

LINAC 104 typically includes one or more of an electron gun for generating electrons, an accelerating waveguide, an electron beam target, an electron beam transport means (such as a bending magnet) for directing the electron beam to the electron beam target, and/or a collimator assembly 208 for collimating and shaping a treatment beam 230 that originates from the electron beam target. Collimator assembly 208 typically includes one or more of a primary collimator that defines the largest available circular radiation field for treatment beam 230, a secondary collimator for providing a rectangular or square radiation field at isocenter 203 (for example via X-jaws and Y-jaws), and a multileaf collimator (MLC) for conforming treatment beam 230 to a PTV or other target volume.

During radiation treatment, in some embodiments LINAC 104 is configured to generate treatment beam 230, which can include high-energy radiation (for example MV X-rays or MV electrons). In other embodiments, treatment beam 230 includes electrons, protons, and/or other heavy charged particles, ultra-high dose rate X-rays (e.g., for FLASH radiotherapy), and/or microbeams for microbeam radiation therapy. In addition, imaging panel 107 is configured to receive imaging radiation and generate suitable projection images therefrom. Further, in some embodiments, as treatment beam 230 is directed to isocenter 203 while C-arm gantry 110 rotates through a treatment arc, image acquisitions can be performed via EPID 105 to generate image data for target volume 209. For example, in such embodiments, EPID 105 generates one or more projection images of target volume 209 and/or a region of patient anatomy surrounding target volume 209. Thus, projection images (e.g., 2D X-ray images) of target volume 209 can be generated during portions of an IGRT or IMRT process via imaging panel 107 and/or EPID 105. Such projection images can then be employed to construct or update portions of imaging data for a digital volume that corresponds to a three-dimensional (3D) region that includes target volume 209. That is, a 3D image of such a 3D region is reconstructed from the projection images. In some embodiments, cone-beam computed tomography (CBCT) and/or digital tomosynthesis (DTS) can be used to process the projection images generated by imaging panel 107.

As noted above, LINAC 104 is configured to generate treatment beam 230 during radiation treatment. For radiation treatments that involve a high radiation dose and/or a small target size, such as stereotactic radiosurgery (SRS) and stereotactic radiotherapy (SRT), the required geometric accuracy of the delivery of treatment beam 230 can be adversely affected by the size, shape, location, and/or asymmetry of the treatment beam penumbra. A treatment beam penumbra is described below in conjunction with FIG. 3.

Figure 3:
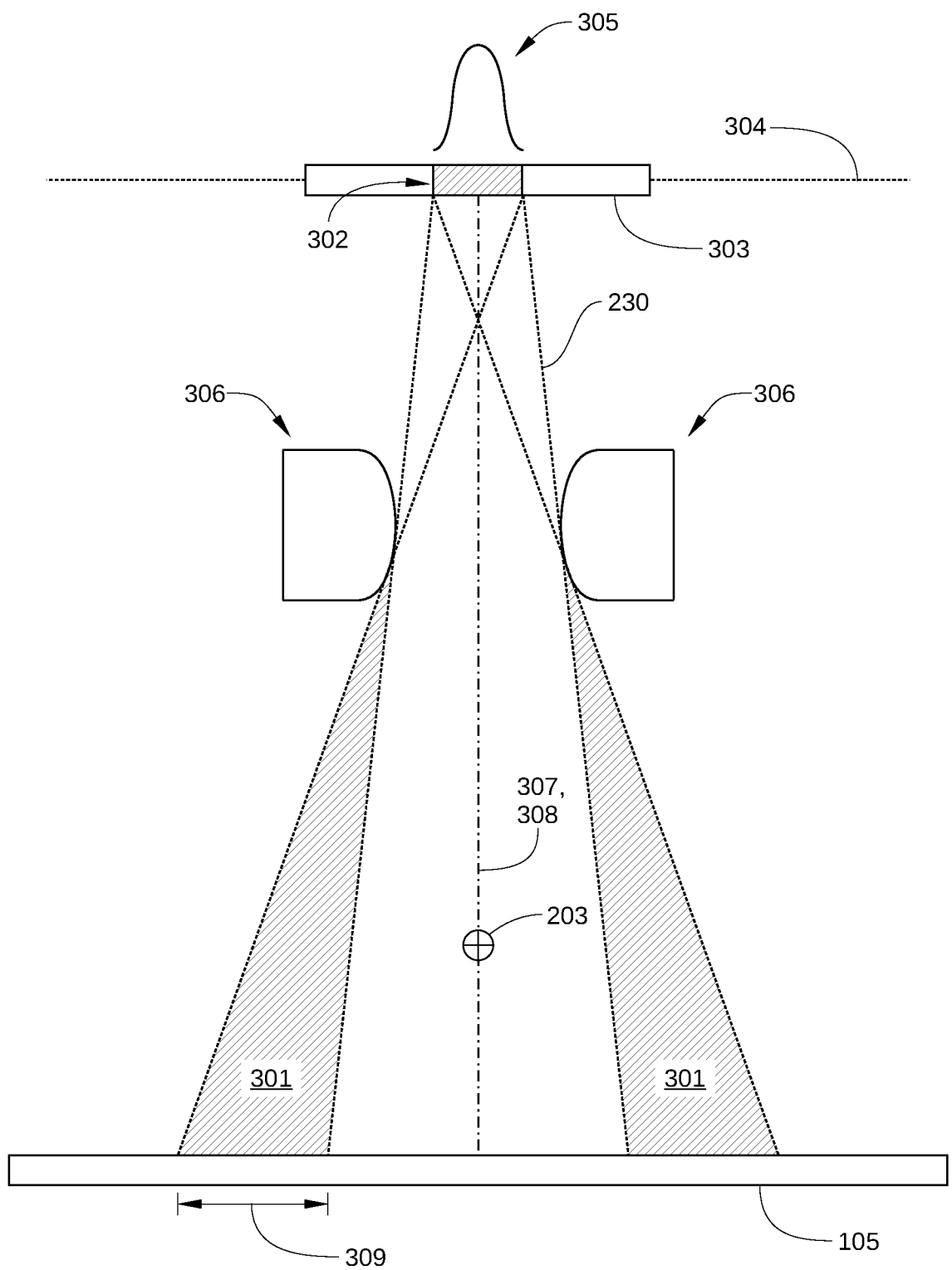
FIG. 3 schematically illustrates a treatment beam with an associated treatment beam penumbra for a particular beam limiting device.

FIG. 3 schematically illustrates treatment beam 230 with an associated treatment beam penumbra 301 for a particular beam-limiting device. As shown, treatment beam 230 is generated by a beam spot 302 (cross-hatched) on an electron beam target 303 that is located in a target plane 304. Beam spot 302 is typically generated by an electron beam (not shown) that is directed onto electron beam target 303 by an accelerating waveguide and electron beam transport means (such as a bending magnet) of LINAC 104. The electron beam creates beam spot 302 on electron beam target 303 from which treatment beam 230 originates. Beam spot 302 has a 3D distribution, which can be quantified via a 2D intensity distribution 305 that represents the electron beam distribution striking electron-beam target 303. 2D intensity distribution 305 is depicted as a one-dimensional function in FIG. 3, but in practice, 2D intensity distribution 305 of beam spot 302 varies over a 2D region of electron beam target 303.

Treatment beam 230 is shaped by one or more MLCs 306 of RT system 100, passes through isocenter 203 of RT therapy system 100, and strikes EPID 105. Ideally, a center axis 307 of treatment beam 230 is aligned with isocenter 203 and with collimator rotation axis 308, about which MLC 306 may rotate. However, even when beam spot 302 is positioned on electron beam target 303 so that center axis 307 of treatment beam 230 is aligned with collimator rotation axis 308 (as shown in FIG. 3), beam spot 302 produces penumbra 301, which is a region at the edge of treatment beam 230 in which there is significant dose fall-off. Penumbra 301 is generated because beam spot 302 is not a single point, but instead is a 2D area on electron beam target 303.

In the instance illustrated in FIG. 3, penumbra 301 is depicted as a geometric penumbra of treatment beam 230. In other instances, penumbra 301, when referenced herein, can further include a transmission penumbra of treatment beam 230, which occurs when a portion of treatment beam 230 passes through an edge of a collimator (e.g., a jaw and/or MLC) before reaching the full attenuation point of the collimator. Thus, in some instances, the term "penumbra" can refer to a geometric penumbra of a treatment beam, a transmission penumbra of a treatment beam, and/or a total penumbra of a treatment beam, which is a combination of the geometric penumbra and the transmission penumbra.

The dose fall-off in a radiation therapy system associated with penumbra 301 can degrade the high spatial accuracy required for certain radiation therapy treatments using treatment beam 230. As a result, radiation therapy systems are typically configured to minimize or otherwise reduce a width 309 of penumbra 301. Further, when beam spot 302 is asymmetric and/or off-center from collimator rotation axis 308 and/or isocenter 203, width 309 generally varies at different portions of penumbra 301, which can complicate conforming treatment beam 230 to a PTV or other target volume. Consequently, precise and accurate knowledge of 2D intensity distribution 305 of beam spot 302 in a radiation therapy system can be highly beneficial, particularly for treatments involving a small PTV and/or a high radiation dose. According to various embodiments, such information regarding 2D intensity distribution 305 can be determined using a conventional radiation therapy system.

Figure 4:
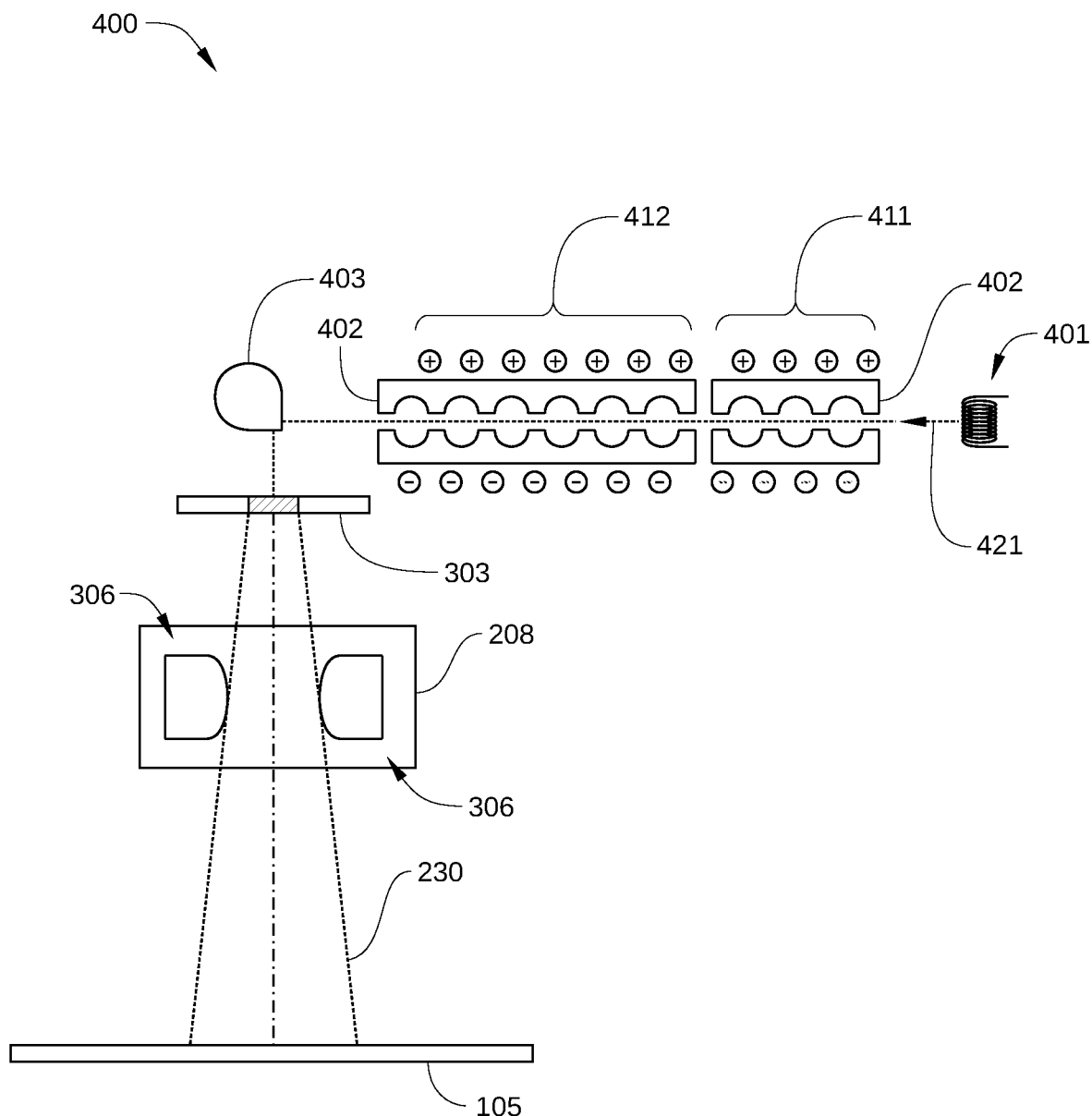
FIG. 4 schematically illustrates a beam-generating subsystem of the radiation therapy system of FIG. 1 that can beneficially implement various embodiments.

FIG. 4 schematically illustrates a beam-generating subsystem 400 of RT system 100 that can beneficially implement various embodiments. Beam-generating subsystem 400 includes components of RT system 100 for generating treatment beam 230 and for generating X-ray projection images of beam spot 302 according to various embodiments. In the embodiment illustrated in FIG. 4, beam-generating subsystem 400 includes LINAC 104, collimator assembly 208, and EPID 105. LINAC 104 includes an electron gun 401 for generating an electron beam 421, an accelerating waveguide 402 for accelerating the electrons of electron beam 421, a first beam-shaping solenoid 411, a second beam-shaping solenoid 412, electron beam target 303, and/or an electron beam transport means (such as a bending magnet) 403. While collimator assembly 208 may typically include one or more of a primary collimator, a secondary collimator, one or more filters, an ionization chamber, MLC 306, and/or other components, for clarity the only portion of collimator assembly 208 shown in FIG. 4 is MLC 306, which is configured to rotate about collimator rotation axis 308. According to various embodiments, a computer-implemented procedure provides a direct measurement of beam spot size, shape, and intensity distribution in RT system 100 using beam-generating subsystem 400. One such embodiment is illustrated below in conjunction with FIG. 5.

Beam Spot Measurement and Analysis

Figure 5:
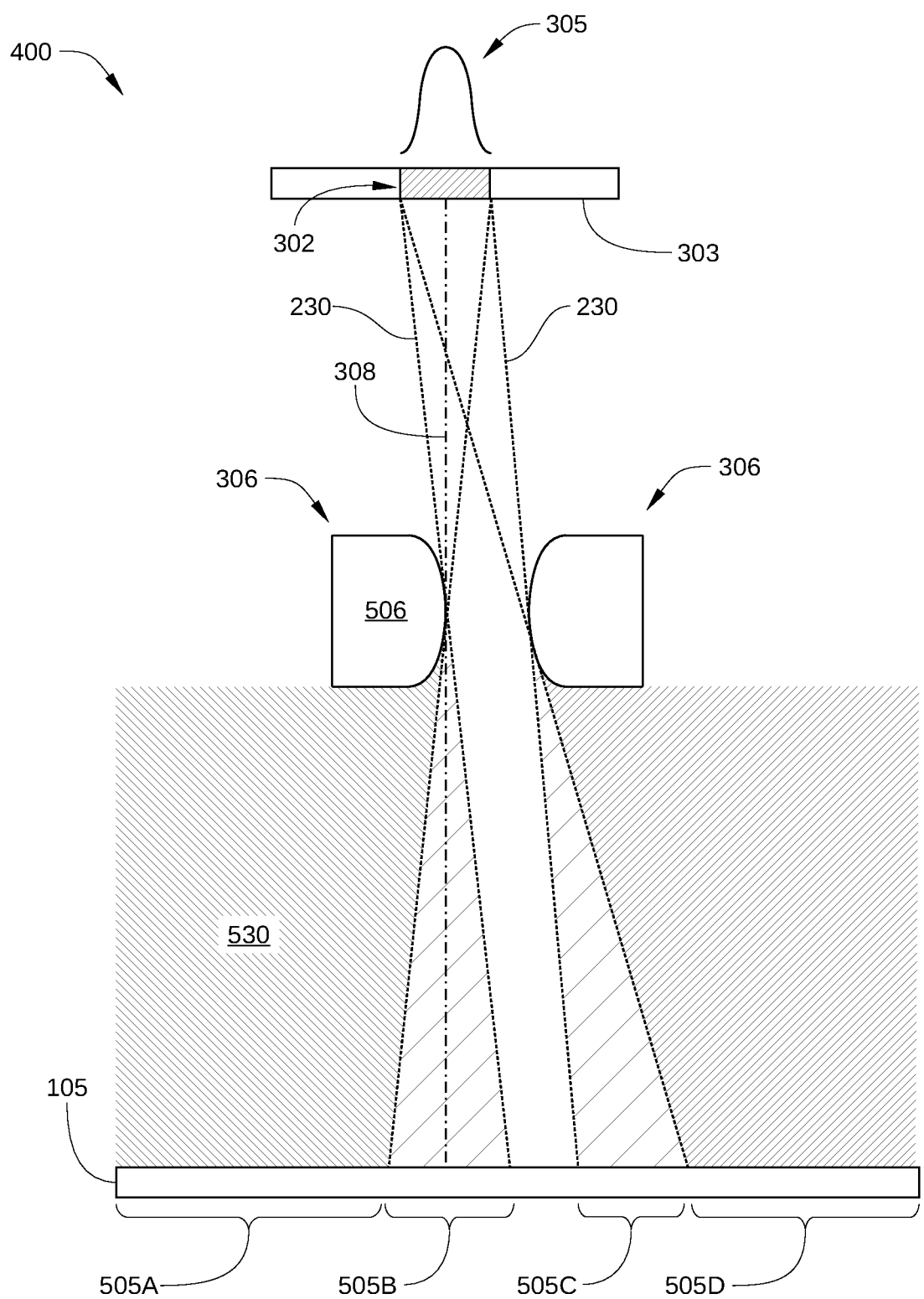
FIG. 5 schematically illustrates a portion of a beam-generating subsystem of the radiation therapy system of FIG. 1 while a beam-spot imaging procedure is performed, according to various embodiments.

FIG. 5 schematically illustrates a portion of beam-generating subsystem 400 while a beam-spot imaging procedure is performed, according to various embodiments. In the embodiments, a direct beam-spot measurement is performed that enables quantification of the size, shape, and location of 2D intensity distribution 305 of beam spot 302. As shown, in the embodiments, a portion 506 of MLC 306 is parked so that a significant portion 530 (e.g., approximately half) of treatment beam 230 is blocked from reaching EPID 105. A sequence of X-ray projection images are then acquired of beam spot 302 with EPID 105 while MLC 306 is rotated about collimator rotation axis 308. Based on the X-ray projection images of the different portions of beam spot 302, an image of beam spot 302 is reconstructed that indicates the size, shape, and location of 2D intensity distribution 305 of beam spot 302. In some embodiments, a reconstruction algorithm (described below in conjunction with FIG. 7) is employed that uses a parallel-beam computed tomography (CT) reconstruction technique to compute the image of beam spot 302.

To generate the sequence of X-ray projection images of beam spot 302, MLC 306 is positioned at a plurality of different rotational angles about collimator rotation axis 308, so that at each different rotational angle, line of sight between beam spot 302 and a different portion of the radiation beam is blocked by portion 506. Further, at each different rotational angle, an X-ray projection image of beam spot 302 is generated with LINAC 104. Thus, for each X-ray projection image, a different portion of beam spot 302 is partially or completely viewable by EPID 105. For example, with MLC 306 positioned as shown in FIG. 5, a first region 505A of EPID 105 does not have line of sight to any of beam spot 302, a second region 505B of EPID 105 has line of sight to a portion of beam spot 302, a third region 505C of EPID 105 has line of sight to a different portion of beam spot 302, and a fourth region 505D of EPID 105 does not have line of sight to any of beam spot 302. As MLC 306 rotates about collimator rotation axis 308, third region 505C and fourth region 505D of EPID 105 have lines of sight to different portions of beam spot 302. Consequently, unless beam spot 302 is perfectly symmetric and precisely centered on collimator rotation axis 308, each such X-ray projection image has a different intensity distribution of received X-rays from beam spot 302. Based on the different intensity distribution of each X-ray projection image of beam spot 302, a 2D image of beam spot 302 can be reconstructed. One embodiment of a 2D image of a beam spot is described below in conjunction with FIG. 6.

Figure 6:
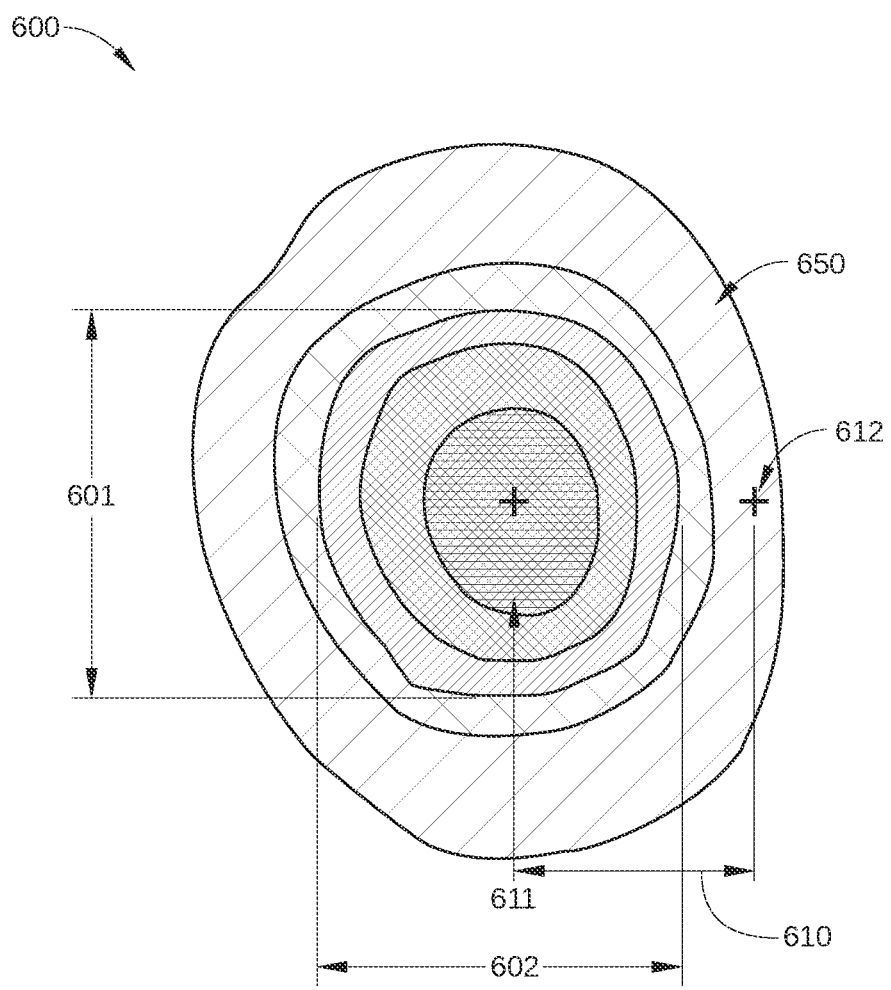
FIG. 6 schematically illustrates a beam spot image, according to various embodiments.

FIG. 6 schematically illustrates a beam spot image 600, according to various embodiments. Beam spot image 600 is an image of a beam spot of a radiation therapy system, such as beam spot 302 of FIG. 3, and is generated using an imager of a conventional radiation therapy system, such as EPID 105 of RT system 100. In the embodiments, beam spot image 600 is reconstructed based on the above-described sequence of projection images of the beam spot and a so-called "edge measurement" algorithm (described below in conjunction with FIG. 7).

As shown in FIG. 6, beam spot image 600 includes a 2D intensity distribution 650 (cross-hatching) of the beam spot depicted by beam spot image 600, where denser cross-hatching indicates a higher intensity of X-rays (or other radiation) being generated. Thus, beam spot image 600 includes information indicating how X-ray radiation intensity varies within a beam spot of a radiation therapy system. In some embodiments, based on such information, one or more beam spot quality metrics are determined for a particular beam spot, including one or more of a beam spot area, a beam spot elongation, a beam spot power per unit area factor, and/or a beam spot center point offset 610.

The beam spot area for a beam spot is a quantified measure of the size of a beam spot and is calculated based on an area of beam spot image 600. In some embodiments, a beam spot area of a beam spot is calculated using all pixels (not shown) in beam spot image 600 that indicate greater than zero radiation intensity. Alternatively, in some embodiments, a beam spot area of a beam spot is calculated using the pixels in beam spot image 600 that indicate a radiation intensity that is greater than a predetermined radiation intensity level. In such embodiments, the predetermined radiation intensity level can be an absolute intensity level or a normalized intensity level, such as a percentage of a peak radiation intensity level indicated in beam spot image 600. For example, in one such embodiment, a beam spot area of a beam spot is calculated using the pixels in beam spot image 600 that indicate a radiation intensity that is greater than 50% of the peak radiation intensity level of beam spot image 600.

The beam spot elongation for a beam spot is a quantified measure of the shape (e.g., roundness and/or symmetry) of a beam spot and is calculated based on attributes of the beam spot visible in beam spot image 600. In some embodiments, a beam spot elongation of a beam spot is calculated using geometrical attributes of the beam spot that are detectable in beam spot image 600, such as a length 601 of a major axis of the beam spot and a length 602 of a minor axis of the beam spot. In such embodiments, the beam spot elongation is the ratio of length 601 and length 602. In such embodiments, length 601 and length 602 may be determined for the entire beam spot visible in beam spot image 600. Alternatively, in such embodiments, length 601 and length 602 are determined for a higher-intensity portion of the beam spot visible in beam spot image 600. For example, in the embodiment illustrated in FIG. 6, length 601 and length 602 are determined for the portion of the beam spot visible in beam spot image 600 that is equal to or greater than 40% of the peak radiation intensity level of beam spot image 600. Thus, in such an embodiment, a lower-intensity portion of beam spot image 600 is ignored in determining length 601 and length 602.

The beam spot power per unit area factor for a beam spot is a quantified measure of the concentration of X-ray-generating power present in a particular beam spot. In some embodiments, the beam spot power per unit area factor for a beam spot quantifies the highest power concentration detected for a particular beam spot. In some embodiments, the beam spot power per unit area factor of a beam spot is calculated based on the beam spot area and on information associated with the electron beam employed to generate the beam spot. In such embodiments, the beam spot area may be calculated as described above, for example using the pixels in beam spot image 600 that indicate a radiation intensity that is greater than a particular percentage of the peak radiation intensity level of beam spot image 600. In some embodiments, the beam spot power per unit area factor of a beam spot is calculated as a ratio of a power value per unit area. In such embodiments, the power value can be based on a peak power of the electron beam employed to generate the beam spot. Further, in such embodiments, the power value can be based on a frequency of the electron beam employed to generate the beam spot and a pulse width of the electron beam employed to generate the beam spot.

Beam spot center point offset 610 is a measure of a distance a center point 611 of a beam spot is located from an ideal center point location 612 of the beam spot. In some embodiments, center point 611 is determined based on the entire beam spot visible in beam spot image 600. Alternatively, in some embodiments, center point 611 is determined based on a higher-intensity portion of the beam spot visible in beam spot image 600, such as the portion of the beam spot visible in beam spot image 600 that is equal to or greater than 40% of the peak radiation intensity level of beam spot image 600. In some embodiments, ideal center point location 612 of the beam spot corresponds to a collimator rotation axis of RT system 100, such as collimator rotation axis 308 in FIG. 3, about which MLC 306 rotates. Thus, in such embodiments, beam spot center point offset 610 may indicate how aligned a center axis of a treatment beam (e.g., center axis 307 in FIG. 3 of treatment beam 230) is with a collimator rotation axis (e.g., collimator rotation axis 308 in FIG. 3). Alternatively, in such embodiments, beam spot center point offset 610 may indicate how aligned beam spot 302 is with a collimator rotation axis or some ideal or optimal location on an electron beam target (e.g., electron beam target 303 in FIG. 3).

As noted above, beam spot image 600 can be reconstructed based on the different intensity distribution of each of the sequence of X-ray projection images generated of beam spot 302 as MLC 306 is rotated about collimator rotation axis 308, as shown in FIG. 3. In some embodiments, an edge measurement algorithm is employed to generate beam spot image 600 of beam spot 302. In such embodiments, the resultant 2D image of beam spot 302 corresponds to a 2D beam spot intensity distribution on electron beam target 303. It is noted that in each X-ray projection image of beam spot 302, the relative intensity of received X-rays at any location in the X-ray projection image depends on how much of beam spot 302 was covered by MLC 506 during acquisition of that X-ray projection image. One such edge measurement algorithm is schematically illustrated in FIG. 7.

Figure 7:
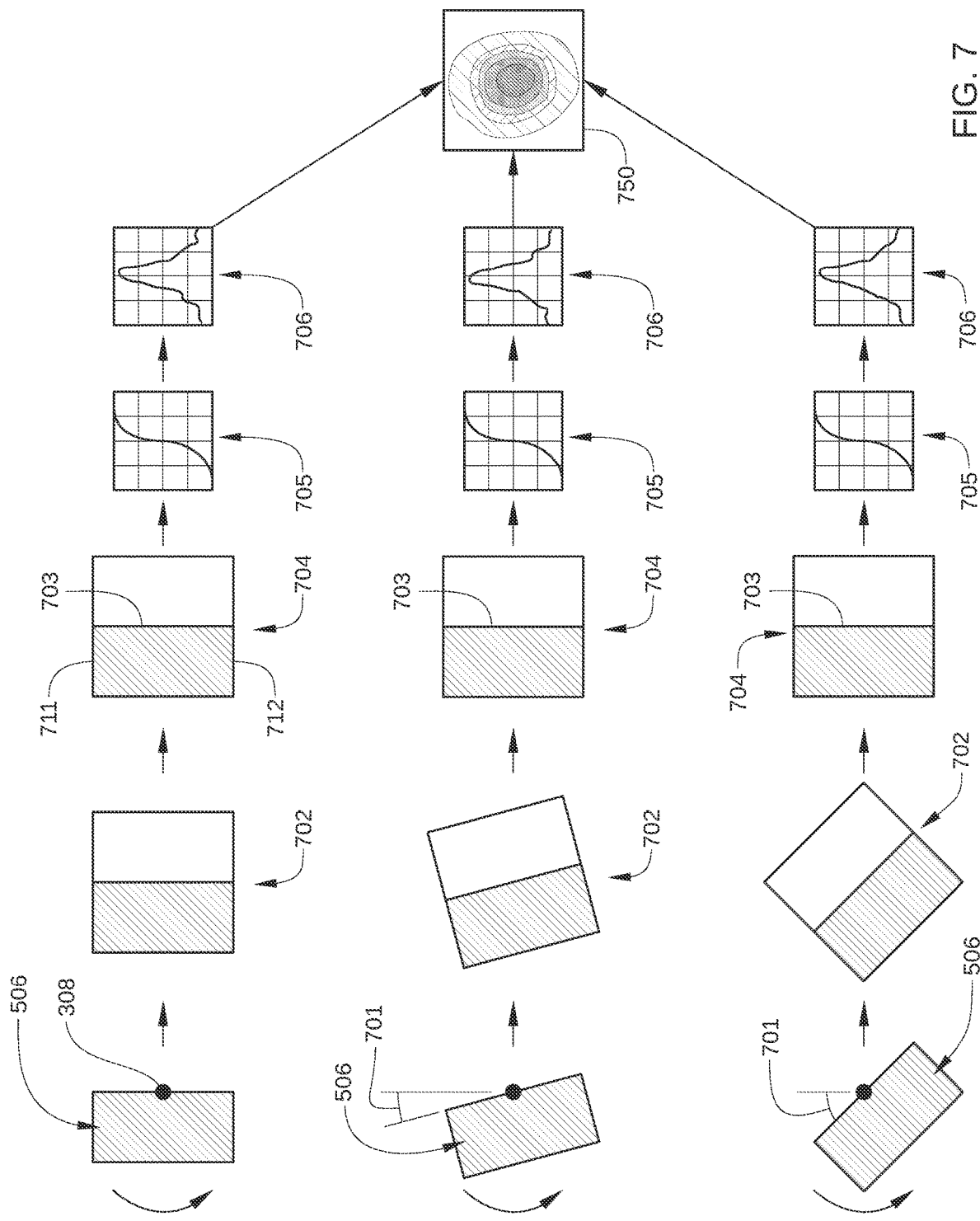
FIG. 7 schematically illustrates various steps of an edge measurement algorithm for generating a 2D image of a beam spot, according to various embodiments.

FIG. 7 schematically illustrates various steps of an edge measurement algorithm for generating a 2D image of beam spot 302, according to various embodiments. As shown, MLC 306 is rotated about collimator rotation axis 308, and at each of a plurality of different rotational angles 701, an X-ray projection image 702 of beam spot 302 is generated with LINAC 104. As part of the edge measurement algorithm, each X-ray projection image 702 of beam spot 302 is rotated to be a rotated X-ray projection image 704, so that an edge 703 formed by portion 506 in each rotated X-ray projection image 704 is oriented in the same way, for example from a top edge 711 of the rotated X-ray projection image 704 to a bottom edge 712 of the rotated X-ray projection image 704. Assuming isotropic radiative emission from every point on beam spot 302, the intensity distribution along any one horizontal row of a rotated X-ray projection image 704 is directly related to the fraction of beam spot 302 that was exposed when the corresponding X-ray projection image 702 was acquired. After averaging over all rows of pixels in a particular rotated X-ray projection image 704, the resulting horizontal intensity distribution is like that of an edge spread function (ESF) 705, one of which is generated for each rotated X-ray projection image 704. A line spread function (LSF) 706 is then generated from each ESF 705 associated with a particular rotated X-ray projection image 704, where LSF 706 for a particular rotated X-ray projection image 704 is a derivative of the ESF 705 for the particular rotated X-ray projection image 704. Thus, for each rotated X-ray projection image 704 of beam spot 302, a different LSF 706 is generated. A sinogram (not shown) is then constructed using the different LSFs 706. When LSFs 706 are available from a sufficient number of projection angles, the sinogram can be used to recover the original 2D intensity distribution 305 of beam spot 302 as a beam spot image 750. A more detailed description of an edge measurement algorithm is described in "Dual Edge Apparatus And Algorithm for Measurement of X-Ray Beam Spot Parameters," Jeung, et al., Med. Phys. 45 (11), November 2018.

In some embodiments, one or more attributes of a beam spot in a radiation therapy system are controlled or otherwise modified based on the 2D intensity distribution determined for the beam spot as described above. In such embodiments, one or more parameters for an electron-beam-shaping component of the radiation system is modified based on the 2D intensity distribution for the beam spot, so that the size, shape, location, and/or intensity distribution of a beam spot is tuned to meet a predetermined specification. One such embodiment is described below in conjunction with FIG. 8.

Figure 8:
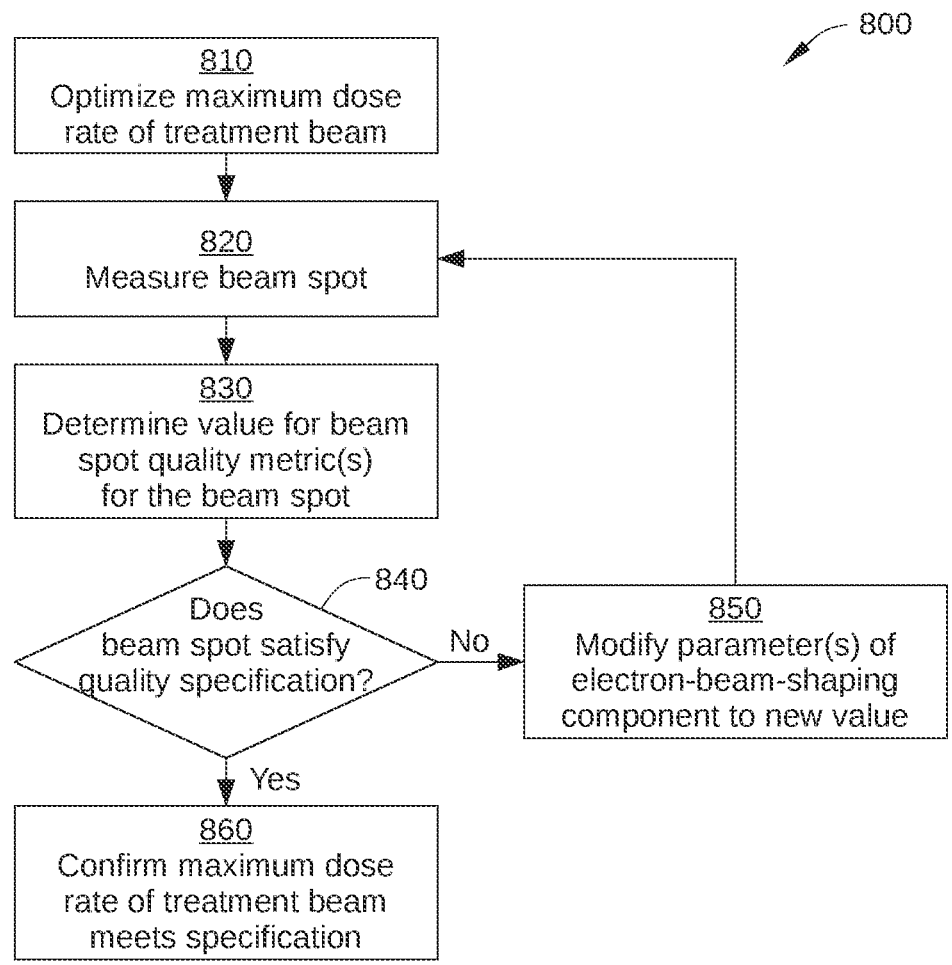
FIG. 8 sets forth a flowchart of a computer-implemented process for tuning a beam spot in a radiation therapy system, according to one or more embodiments.

FIG. 8 sets forth a flowchart of a computer-implemented process 800 for tuning a beam spot in a radiation therapy system, according to one or more embodiments. Computer-implemented process 800 can be performed as a part of factory setup of a radiation therapy system, as an on-site quality-assurance tool for the radiation therapy system, and/or as a periodic service tool for the radiation therapy system.

Computer-implemented process 800 may include one or more operations, functions, or actions as illustrated by one or more of blocks 810-860. Although the blocks are illustrated in a sequential order, these blocks may be performed in parallel, and/or in a different order than those described herein. Also, the various blocks may be combined into fewer blocks, divided into additional blocks, and/or eliminated based upon the desired implementation. Although computer-implemented process 800 is described in conjunction with the X-ray imaging system described herein as part of RT system 100 and FIGS. 1-5, persons skilled in the art will understand that any suitably configured X-ray imaging system is within the scope of the present embodiments.

The control algorithms for the blocks of computer-implemented process 800 may be performed by any suitable computing device or devices. For example, in some embodiments, some or all of the control algorithms for the blocks of computer-implemented process 800 reside in image acquisition and treatment control computer 109, remote control console 111, a combination of both, or any other computing device communicatively coupled to RT system 100. The control algorithms can be implemented in whole or in part as software- or firmware-implemented logic, and/or as hardware-implemented logic circuits.

In step 810, a suitable computing device causes optimization of a particular treatment beam to be performed. In some embodiments, such treatment beam optimization includes confirming a maximum dose rate of treatment beam 230 using conventional techniques known in the art. In addition, in some embodiments, such treatment beam optimization further includes modifying one or more beam-generation parameters associated with the dose rate of treatment beam 230 for the particular configuration of treatment beam 230 until the particular treatment beam 230 is confirmed to have a specified dose rate. In some embodiments, the one or more beam-generation parameters include electron gun current, RF power, energy switch position, one or more bending magnet parameters, one or more gun driver parameters, and/or the like. In some embodiments, the maximum dose rate of treatment beam 230 includes a margin above a maximum specified dose rate that is used in practice. When treatment beam 230 is confirmed to provide a suitable maximum dose rate, the optimization of treatment beam 230 is complete and computer-implemented process 800 proceeds to step 820.

In step 820, the computing device causes beam spot 302 of RT system 100 to be measured, for example by the acquisition of a sequence of X-ray projection images of beam spot 302 and the application of an edge measurement algorithm, as described above in conjunction with FIG. 5. In some embodiments, the output of such an algorithm includes a 2D intensity distribution 305 of beam spot 302. In some embodiments, the output of such an algorithm includes information indicating a location of a beam spot center point 611, for example relative to an absolute position on electron beam target 303.

In step 830, the computing device determines a value for one or more beam spot quality metrics for beam spot 302, based on the output of step 820. In some embodiments, the one or more beam spot quality metrics include a beam spot area, a beam spot elongation, a beam spot power per unit area factor, and/or a beam spot center point offset from an ideal center point location, among others.

In step 840, the computing device determines whether beam spot 302 satisfies a predetermined beam spot quality specification. When the computing device determines that beam spot 302 satisfies the predetermined beam spot quality specification, computer-implemented process 800 proceeds to step 860. When the computing device determines that beam spot 302 fails to satisfy the predetermined beam spot quality specification, computer-implemented process 800 proceeds to step 850.

In some embodiments, in step 840 the computing device determines whether beam spot 302 satisfies the predetermined beam spot quality specification based on one or more beam spot quality metrics. For example, in one such embodiment, the computing device determines whether beam spot 302 satisfies the predetermined beam spot quality specification based on an eccentricity of beam spot 302. In such an embodiment, when a value determined in step 830 for the eccentricity of beam spot 302 is less than a threshold eccentricity value (such as a specified maximum acceptable eccentricity for beam spot 302), the computing device determines that beam spot 302 satisfies the predetermined beam spot quality specification. In another example, in an embodiment, the computing device determines whether beam spot 302 satisfies the predetermined beam spot quality specification based on a size (e.g., area) of eccentricity of beam spot 302. In such an embodiment, when a value determined in step 830 for the area of beam spot 302 is less than a threshold maximum value (such as a specified maximum acceptable area for beam spot 302), and is greater than a threshold minimum value (such as a specified minimum acceptable area for beam spot 302), the computing device determines that beam spot 302 satisfies the predetermined beam spot quality specification. In yet another example, in an embodiment, the computing device determines whether beam spot 302 satisfies the predetermined beam spot quality specification based on a power per unit area of beam spot 302. In such an embodiment, when a value determined in step 830 for the area of beam spot 302 is greater than a threshold maximum value (such as a specified maximum acceptable power per unit area for beam spot 302), the computing device determines that beam spot 302 does not satisfy the predetermined beam spot quality specification.

In some embodiments, in step 840 the computing device determines whether beam spot 302 satisfies the predetermined beam spot quality specification based multiple beam spot quality metrics. For example, in some embodiments, when the value determined in step 830 for each of the multiple beam spot quality metrics satisfies a respective specified threshold or thresholds, the computing device determines that beam spot 302 satisfies the predetermined beam spot quality specification. In such embodiments, failure of a single value determined in step 830 to satisfy a respective specified threshold or thresholds indicates that beam spot 302 fails to satisfy the predetermined beam spot quality specification. Alternatively, in some embodiments, failure of one or more values determined in step 830 to satisfy a respective specified threshold or thresholds may not indicate that beam spot 302 fails to satisfy the predetermined beam spot quality specification. Instead, in such embodiments, a weighting scheme for each beam spot quality metric may be employed to quantify how well each particular beam spot quality metric is satisfied. In such embodiments, an overall quality score for beam spot 302 is determined that is based on such a weighting scheme as applied to the multiple values determined in step 830. In such embodiments, a particular beam spot 302 may have an overall quality score indicating that the particular beam spot 302 satisfies the predetermined beam spot quality specification even though a value for one or more beam spot quality metrics determined in step 830 may not satisfy an associated threshold value for each of the one or more beam spot quality metrics. Further, in such embodiments, each beam spot quality metric may have a different score weighting, depending on the relative importance of each beam spot quality metric.

In some embodiments, a predetermined beam spot quality specification may include multiple threshold values for one or more beam spot quality metrics for beam spot 302. In such embodiments, for a particular beam spot quality metric, the predetermined beam spot quality specification may include an upper threshold value and a lower threshold value for beam spot 302. In such embodiments, the lower threshold value for a particular beam spot quality metric may indicate an ideal threshold that beam spot 302 may, but is not required to, satisfy. By contrast, the upper threshold value for the particular beam spot quality metric may indicate an undesired value at which beam spot 302 fails to satisfy the predetermined beam spot quality specification, regardless of the overall quality score for beam spot 302 with respect to other beam quality metrics. That is, in such embodiments, failure of beam spot 302 to satisfy the upper threshold indicates that the beam spot is not suitable for use and should be modified. Alternatively, in some embodiments, the upper threshold value for a particular beam spot quality metric indicates a value at which beam spot 302 accrues a more severe scoring penalty (higher scoring penalty or lower reward) than that associated with the lower threshold value for that particular beam spot quality metric. Alternatively, in some embodiments, the above-described roles of the upper threshold value and the lower threshold value for a particular beam spot quality metric are reversed, i.e., the upper threshold value for a particular beam spot quality metric indicate an ideal threshold value and the lower threshold value for the particular beam spot quality metric beam spot 302 indicates an undesired (or more heavily penalized) threshold value for the particular beam spot quality metric. For example, in the case of an area coincidence factor (described below in conjunction with FIGS. 10A-10C), a lower threshold value may indicate an undesired value for a beam spot.

In step 850, the computing device modifies one or more parameters of an electron-beam-shaping component of RT system 100 to a new value. As a result, one or more attributes of beam spot 302 are changed that affect 2D intensity distribution 305 of beam spot 302, such as an eccentricity of beam spot 302, an average diameter of beam spot 302, an offset distance of beam spot 302, a size or area of beam spot 302, a power per unit area of beam spot 302, and/or the like. In some embodiments, the one or more parameters modified in step 850 are selected based on which of the one or more beam spot quality metrics of the predetermined beam spot quality specification beam spot 302 failed to satisfy in step 840. Upon completion of step 850, computer-implemented process 800 returns to step 820 and the computing device causes beam spot 302 of RT system 100 to be measured again.

Examples of parameters of an electron-beam-shaping component of RT system 100 include a solenoid current for first beam-shaping solenoid 411, a solenoid current for second beam-shaping solenoid 412, a direction of current flow in first beam-shaping solenoid 411, a direction of current flow in second beam-shaping solenoid 412, and/or the like. Because the direction and magnitude of current flowing through first beam-shaping solenoid 411 and second beam-shaping solenoid 412 can affect the electron beam that generates beam spot 302 (and therefore treatment beam 230), modification of such parameters also alters one or more attributes of beam spot 302. Alternatively or additionally, in some embodiments, parameters of other beam-shaping components of RT system 100 are modified in step 850 to alter one or more attributes of beam spot 302. Examples of other beam-shaping components of RT system 100 include electron gun 401, accelerating waveguide 402, and/or electron beam transport means 403.

In step 860, the computing device confirms that the maximum dose rate of treatment beam 230 continues to have a specified maximum dose rate. In instances in which the maximum dose rate of treatment beam is below the specified maximum dose rate, one or more beam-generation parameters associated with the dose rate of treatment beam 230 are modified until treatment beam 230 is confirmed to have a specified dose rate. Upon completion of step 860, computer-implemented process 800 ends.

In some embodiments, steps 820-850 are performed over multiple iterations until specified attributes of treatment beam 230 satisfy a predetermined beam spot quality specification. Because each such iteration can be completed in an automated fashion in a relatively short time (e.g., 1-5 minutes) and without the use of equipment and/or measuring instruments external to RT system 100, a particular treatment beam 230 can be tuned in a short time, for example in a fraction of an hour. Further, computer-implemented process 800 can be performed for each of a plurality of treatment beam energies that may be employed by RT system 100. Because computer-implemented process 800 can be completed so quickly, computer-implemented process 800 can be performed as a part of factory setup of a radiation therapy system, as an on-site quality-assurance tool for the radiation therapy system, and/or as a periodic service tool for the radiation therapy system.

Implementation of computer-implemented process 800 enables precise control of beam spot shape and size in RT system 100, thereby ensuring consistency in a pre-configured treatment beam 230. Thus, treatment beam 230 can meet tight the geometric tolerances and small field penumbra required for forms of radiation therapy that involve delivery of a high radiation dose to a small focused region of a patient's anatomy. Further, treatment beam 230 can be assumed to have substantially the same attributes of the ideal treatment beam employed in treatment planning models.

Radiation Field Measurement and Analysis

In the embodiments described above, direct measurement of a beam spot enables tuning of one or more attributes of the beam spot in a radiation therapy system. For example, based on such beam spot measurements, one or more beam-shaping parameters that affect generation of the beam spot are modified so that the one or more attributes of the beam spot are changed. In other embodiments, measurement of one or more attributes of a radiation field generated by a beam spot enables similar tuning of the beam spot. In such embodiments, one or more beam-shaping parameters are modified based on the measured attributes of the radiation field, so that the one or more attributes of the beam spot are changed. The attributes of the radiation field are quantified via one or more specific radiation field quality metrics that indicate whether a radiation beam originating from the beam spot is outside a specified quality range. Examples of such radiation field quality metrics include one or more of an area coincidence factor, a penumbra asymmetry factor, and a beam output factor.

In some embodiments, values for one or more radiation field quality metrics are measured based on images that are generated using an existing imaging panel of the radiation therapy system, such as EPID 105 of RT system 100. In such embodiments, one or more slit-field images are employed, in which a treatment beam (e.g., treatment beam 230 in FIG. 2) originating from a beam spot (e.g., beam spot 302 in FIG. 3) is shaped via a narrow rectangular aperture and imaged by EPID 105. For example, the narrow rectangular aperture can be formed by an MLC of the radiation therapy system, such as MLC 306 of RT system 100. As the MLC is rotated about a rotational axis, a different slit-field image is generated with the MLC at a different rotational orientation relative to the imaging panel. Quantitative analysis of the different slit-field images, as described herein, enables determination of the symmetry of a radiation field generated by a particular beam spot. One embodiment of an aperture for generating slit-field images is described below in conjunction with FIG. 9, and one embodiment of a slit-field image is described below in conjunction with FIG. 10.

Figure 9:
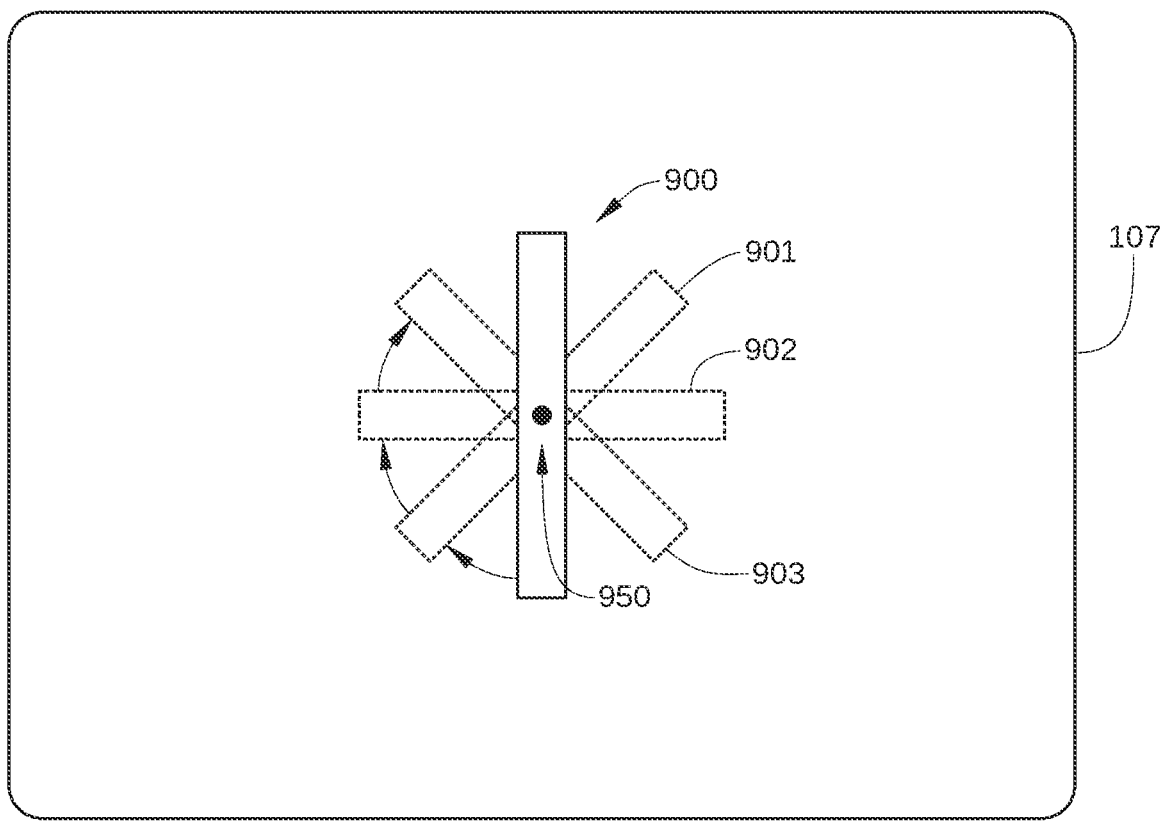
FIG. 9 schematically illustrates an aperture 900 and imager 910 for generating slit-field images, according to various embodiments.

FIG. 9 schematically illustrates an aperture 900 and imager 910 for generating slit-field images, according to various embodiments. In the embodiment illustrated in FIG. 9, aperture 910 is formed by an MLC of a radiation therapy system, such as MLC 306 in FIG. 3, and imager 910 is an imager included in the radiation therapy system, such as EPID 105 of RT system 100. Aperture 900 and imager 910 are shown in a "beam's-eye" view in FIG. 9, which is from the perspective of a source of a treatment beam, such as LINCAC 104 of RT system 100.

In the embodiment illustrated in FIG. 9, multiple additional orientations of aperture 900 with respect to imager 910 are shown that can each be employed to generate a slit-field image. The additional orientations include an orientation 901, in which the MLC is positioned at a rotational angle of 45° about an axis of rotation 950 of the collimator, an orientation 902, in which the MLC is positioned at a rotational angle of 90° about axis of rotation 950, and an orientation 903, in which the MLC is positioned at a rotational angle of 135° about the axis of rotation 950. In other embodiments, more or fewer orientations of aperture 900 may be employed to generate slit-field images.

Figure 10:
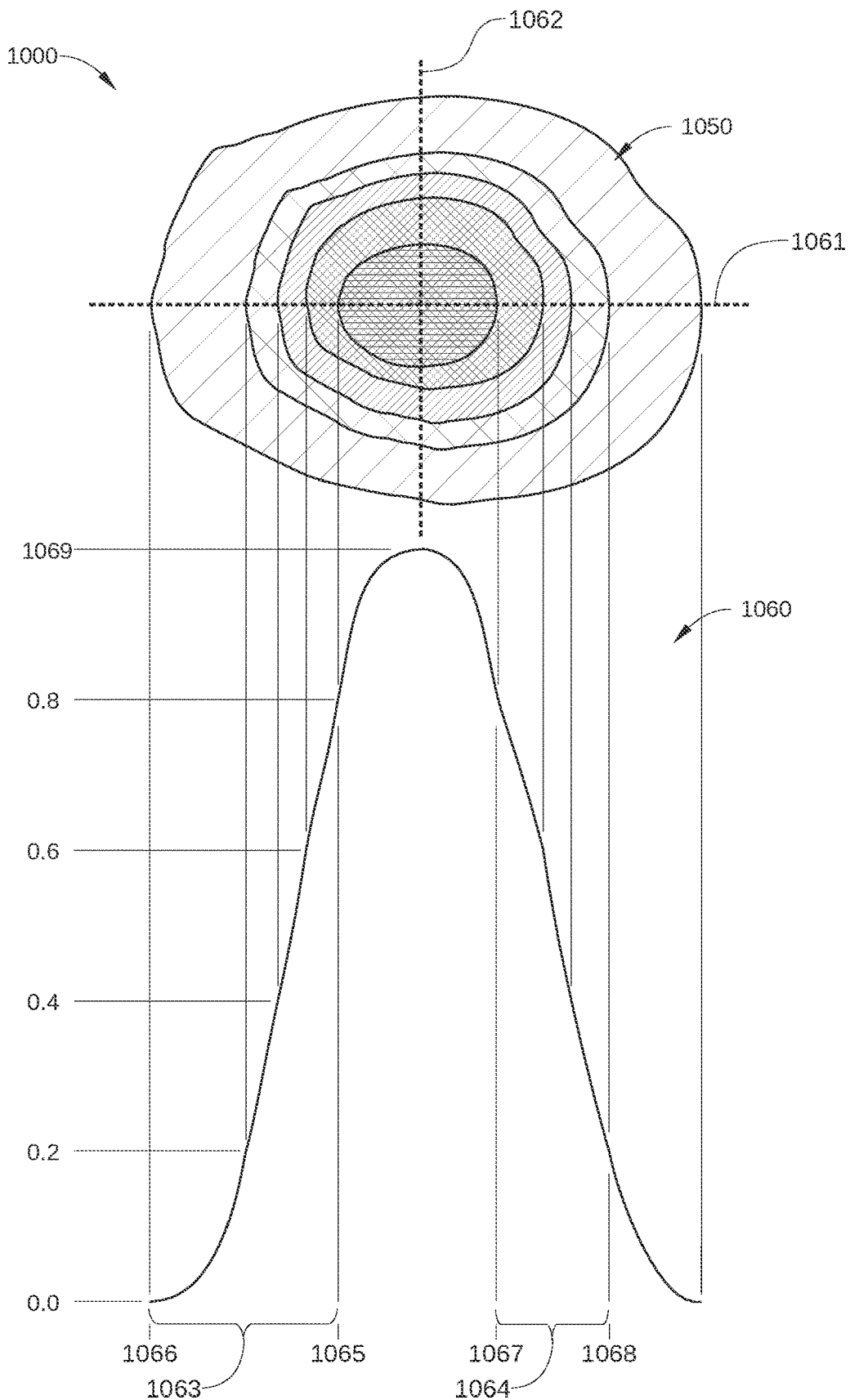
FIG. 10 schematically illustrates a slit-field X-ray image and an associated penumbra and output factor, according to various embodiments.

FIG. 10 schematically illustrates a slit-field X-ray image 1000 and an associated penumbra and output factor, according to various embodiments. Slit-field X-ray image 1000 is an X-ray image generated using a treatment beam, an imager, and an MLC of a conventional radiation therapy system, such as treatment beam 230, EPID 105, and MLC 306 of RT system 100. In some embodiments, slit-field image 1000 is generated with EPID 105 positioned at or near isocenter 203 of RT system 100 rather than at a position employed during radiation treatment. In such embodiments, the added complication of treatment beam 230 and the associated penumbra being magnified is avoided.

As shown in FIG. 10, slit-field X-ray image 1000 includes a 2D intensity distribution 1050 of the radiation intensity, depicted by cross-hatching, where denser cross-hatching indicates a higher intensity of X-rays being received by EPID 105. Thus, slit-field X-ray image 1000 includes information indicating how X-ray radiation intensity varies within a particular treatment beam 230, such as a treatment beam that has a beam size similar to the width of the rectangular aperture employed to generate slit-field X-ray image 1000. In some embodiments, based on such information, one or more radiation field quality metrics are determined for a particular beam spot and aperture combination, including one or more of an area coincidence factor, a penumbra asymmetry factor, and an X-ray beam output factor. In the embodiments, values for the one or more radiation field quality metrics are compared to corresponding values of a predetermined radiation field quality specification to determine whether a treatment beam that generates slit-field X-ray image 1000 is outside a specified quality range.

FIG. 10 further includes a one-dimensional X-ray intensity profile 1060 that depicts X-ray dose along a linear portion 1061 of slit-field X-ray image 1000. Thus, X-ray intensity profile 1060 indicates how radiation intensity varies across 2D intensity distribution 1050 of slit-field X-ray image 1000. In some embodiments, linear portion 1061 is oriented along a major axis of slit-field X-ray image 1000. That is, linear portion 1061 is oriented parallel to the rectangular aperture employed to generate slit-field X-ray image 1000. Alternatively or additionally, a one-dimensional X-ray intensity profile can be generated for other linear portions of slit-field X-ray image 1000, such as along a minor axis 1062 (which is perpendicular to the rectangular aperture employed to generate slit-field X-ray image 1000). Further, in the embodiment illustrated in FIG. 10, X-ray intensity profile 1060 is normalized to a peak X-ray intensity value 1069 of one-dimensional X-ray intensity profile 1060. Various radiation field quality metrics (area coincidence factor, penumbra asymmetry factor, and X-ray beam output factor) are now described with respect to slit-field X-ray image 1000.

The penumbra asymmetry factor is a quantified measure of the symmetry of the penumbra of an X-ray beam, such as an X-ray beam used to generate slit-field X-ray image 1000. In some embodiments, the penumbra asymmetry factor for an X-ray beam is based on a difference between a first penumbra portion 1063 of one-dimensional X-ray intensity profile 1060 and a second penumbra portion 1064 of one-dimensional X-ray intensity profile 1060. In such embodiments, first penumbra portion 1063 is disposed on a first side of one-dimensional X-ray intensity profile 1060, and second penumbra portion 1064 is disposed on a second side of one-dimensional X-ray intensity profile 1060, where the first side is opposite the second side as shown in FIG. 10.

In the embodiment illustrated in FIG. 10, first penumbra portion 1063 is defined as a width between a location 1065 of a radiation intensity that corresponds to a beginning of a penumbra fall-off region on the first side of one-dimensional X-ray intensity profile 1060 and a location 1066 of a radiation intensity that corresponds to an ending of the penumbra fall-off region on the first side of one-dimensional X-ray intensity profile 1060. Similarly, second penumbra portion 1064 is defined as a width between a location 1067 of the radiation intensity that corresponds to the beginning of the penumbra fall-off region on the second side of one-dimensional X-ray intensity profile 1060 and a location 1068 of the radiation intensity that corresponds to the ending of the penumbra fall-off region on the second side of one-dimensional X-ray intensity profile 1060. For example, in the embodiment illustrated in FIG. 10, the radiation intensity that corresponds to the beginning of the penumbra fall-off region (locations 1065 and 1067) is 80% of peak radiation intensity level 1069 of one-dimensional X-ray intensity profile 1060, and the radiation intensity that corresponds to the ending of the penumbra fall-off region (locations 1066 and 1068) is 20% of peak radiation intensity level 1069. In other embodiments, the radiation intensities that correspond to the beginning and ending of the penumbra fall-off region can vary from those shown in FIG. 10.

The X-ray beam output factor is a quantified measure of the radiation intensity associated with the X-ray beam that generates slit-field X-ray image 1000 relative to a reference X-ray beam. In some embodiments, the X-ray beam output factor is a ratio of the radiation intensity associated with the X-ray beam of interest and the reference X-ray beam. Generally, the reference X-ray beam has a larger field than the X-ray beam that generates slit-field X-ray image 1000. For example, in an embodiment, the X-ray beam that generates slit-field X-ray image 1000 has a field size of about 4 mm×7.5 mm, and the reference X-ray beam has a field size of about 10 cm×10 cm. As a result, the X-ray beam output factor for an X-ray beam that generates slit-field X-ray image 1000 is generally less than 1. In some embodiments, for a specific combination of rectangular aperture and treatment beam 230 that generates slit-field X-ray image 1000, the X-ray beam output factor is calculated for multiple orientations of the rectangular aperture (e.g., 0°, 45°, 90°, and 135°) around the beam collimator axis.

The area coincidence factor is a quantified measure of the variation in shape of a dose cloud of the X-ray beam that generates slit-field X-ray image 1000. The dose cloud is the geometrical enclosure of points with a dose larger or equal to a predefined intensity (e.g. an 80% isodose contour). Specifically, the area coincidence factor quantifies the variation in shape of such a dose cloud as the rectangular aperture that forms the X-ray beam rotates through different angles. Thus, in some embodiments, for a particular treatment beam 230 and rectangular aperture, multiple values for the area coincidence factor are determined. For example, in one such embodiment, for the particular treatment beam 230 and rectangular aperture, a different value for the area coincidence factor is determined for each of multiple orientations of the rectangular aperture (e.g., 0°, 45°, 90°, and 135°). One such embodiment is described below in conjunction with FIGS. 11A-11C.

Figure 11A:
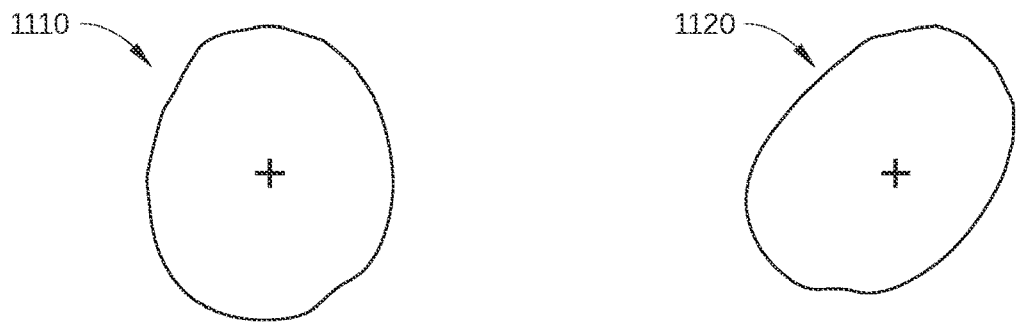
FIG. 11A-11C schematically illustrate determination of an area coincidence factor for a particular combination of a treatment beam, aperture, and aperture orientation, according to various embodiments.
Figure 11B:
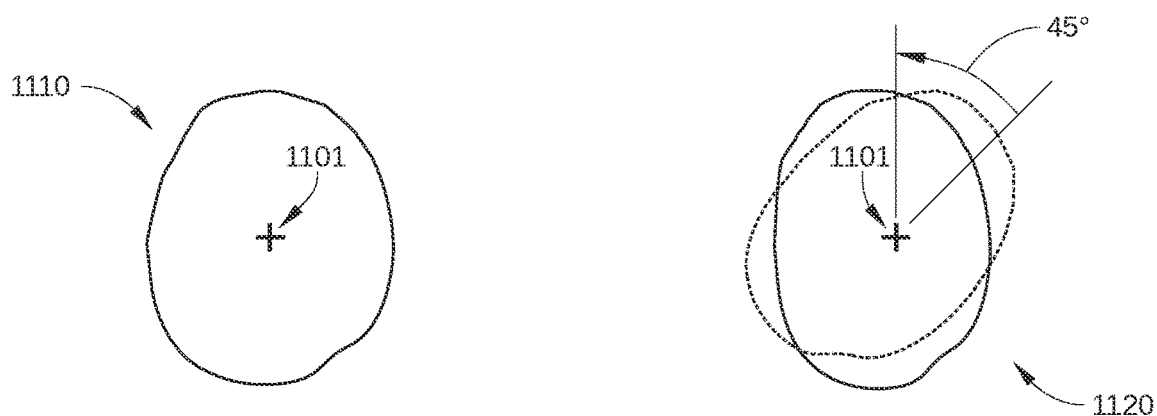
Figure 11C:
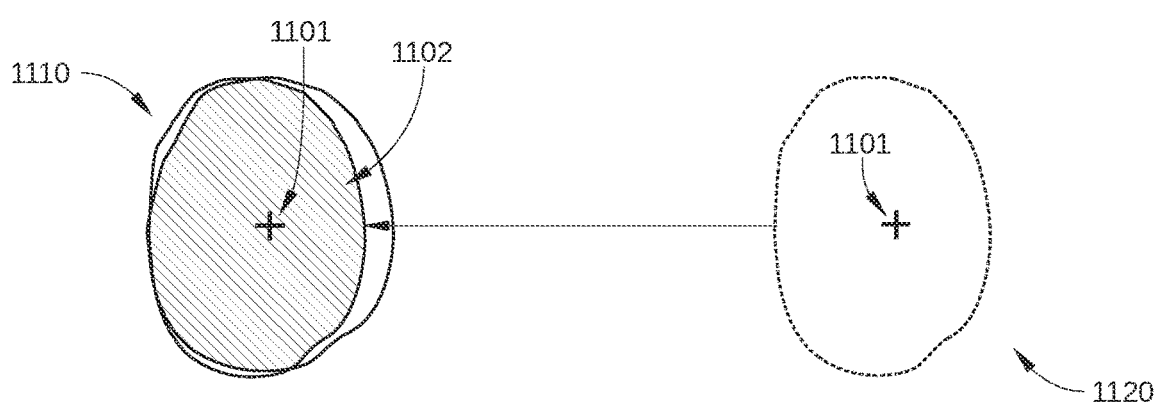

FIGS. 11A-11C schematically illustrate determination of an area coincidence factor for a particular combination of treatment beam 230, rectangular aperture, and aperture orientation, according to various embodiments. FIG. 11A illustrates a first step in a process of generating the area coincident factor for the particular combination of treatment beam 230 and rectangular aperture; FIG. 11B illustrates a second step in the process of generating the area coincident factor; and FIG. 11C illustrates a third step in the process of generating the area coincident factor.

FIG. 11A shows a reference dose cloud 1110 and an evaluated dose cloud 1120 after acquisition of slit-field X-ray images 900 using the particular combination of treatment beam 230 and rectangular aperture. In the embodiment illustrated in FIG. 11A, reference dose cloud 1110 is based on a reference slit-field X-ray image (not shown) generated with the rectangular aperture oriented at 0°, and evaluated dose cloud 1120 is based on an evaluated slit-field X-ray image (not shown) generated with the rectangular aperture oriented at 45°. Further, in the embodiment illustrated in FIG. 11A, reference dose cloud 1110 corresponds to a portion of the reference slit-field X-ray image that represents a radiation intensity of 60% or more of a peak radiation intensity of the reference slit-field X-ray image. Thus, reference dose cloud 1110 does not include portions of the reference slit-field X-ray image that indicate a radiation intensity of less than 60% of the peak radiation intensity of the reference slit-field X-ray image. Likewise, in FIG. 11A, evaluated dose cloud 1120 corresponds to a portion of the evaluated slit-field X-ray image that represents a radiation intensity of 60% or more of a peak radiation intensity of the evaluated slit-field X-ray image. Thus, evaluated dose cloud 1120 does not include portions of the evaluated slit-field X-ray image that indicate a radiation intensity of less than 60% of the peak radiation intensity of the evaluated slit-field X-ray image. In other embodiments, reference dose cloud 1110 and evaluated dose cloud 1120 are defined based on a higher or lower radiation intensity cut-off than the 60% level illustrated in FIGS. 11A—11C (e.g., 80% of a peak radiation intensity, 50% of a peak radiation intensity, etc.).

FIG. 11B shows evaluated dose cloud 1120 after being rotated to align with reference dose cloud 1110. Thus, in the embodiment illustrated in FIG. 11B, evaluated dose cloud 1120 is rotated 45° as shown, since evaluated dose cloud 1120 is based on an evaluated slit-field X-ray image generated with the rectangular aperture oriented at 45°. In such embodiments, the area coincidence factor determined for evaluated dose cloud 1120 enables variation in the shape of evaluated dose cloud 1120 from reference dose cloud 1110 to be captured, as shown in FIG. 11C.

In addition, in some embodiments, to align evaluated dose cloud 1120 with reference dose cloud 1110, evaluated dose cloud 1120 is rotated about a beam center point 1101, which corresponds to an ideal center point of a treatment beam. For example, in some embodiments, beam center point 1101 corresponds to a collimator rotation axis (such as collimator rotation axis 308 in FIG. 3). Alternatively, beam center point 1101 corresponds to some other absolute position on the imager that generates the reference slit-field X-ray image and the evaluated slit-field X-ray image (e.g., EPID 105 of FIG. 2). In such embodiments, beam center point 1101 does not necessarily correspond to a center point (such as the centroid) of reference dose cloud 1110 or of evaluated dose cloud 1120. In such embodiments, the area coincidence factor determined for evaluated dose cloud 1120 captures the difference in the position of evaluated dose cloud 1120 (e.g., relative to beam center point 1101) from the position of reference dose cloud 1110. That is, when evaluated dose cloud 1120 is offset a different distance from beam center point 1101 than reference dose cloud 1110, the area coincidence factor quantitatively captures the resulting reduction in coincidence (illustrated in FIG. 11C) between evaluated dose cloud 1120 and reference dose cloud 1110.

FIG. 11C shows evaluated dose cloud 1120 after being superimposed onto reference dose cloud 1110. In some embodiments, evaluated dose cloud 1120 is superimposed onto reference dose cloud 1110 based on the location of beam center point 1101 in reference dose cloud 1110 and in evaluated dose cloud 1120. In FIG. 11C, an area of coincidence 1102 (cross-hatching) indicates a portion of evaluated dose cloud 1120 that coincides with reference dose cloud 1110. It is noted that differences in shape and in position relative to beam center point 1101 can both contribute to a smaller area of coincidence 1102 between reference dose cloud 1110 and evaluated dose cloud 1120. In some embodiments, a value of the area coincidence factor determined for a particular evaluated dose cloud 1120 is a normalized value based on area of coincidence 1102 and a total area of either reference dose cloud 1110 or evaluated dose cloud 1120. Thus, in such embodiments, the value of the area coincidence factor determined for a particular evaluated dose cloud 1120 is generally between 0 and 1.

Figure 12:
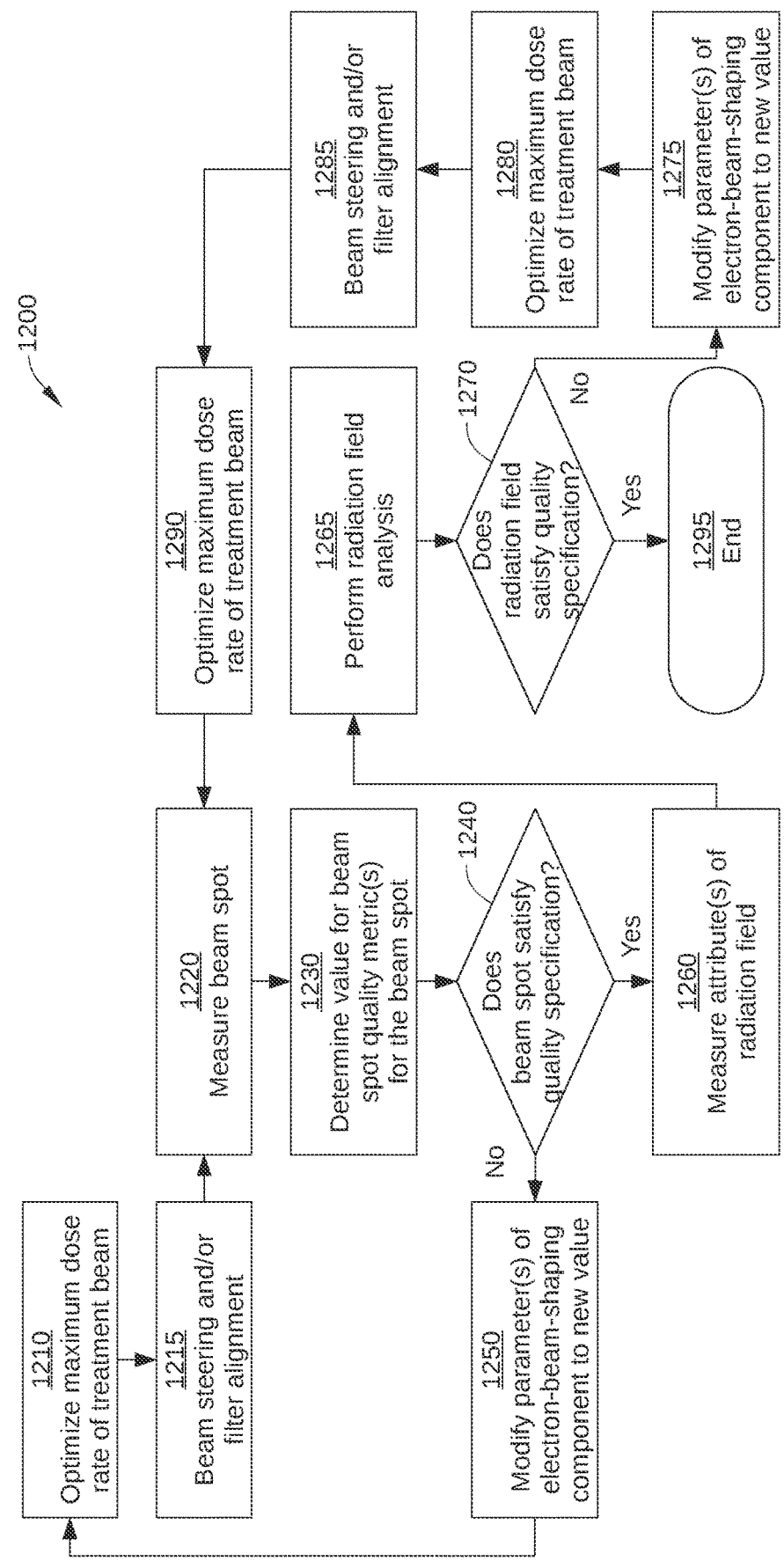
FIG. 12 sets forth a flowchart of a computer-implemented process for tuning a beam spot in a radiation therapy system based on measurements of a radiation field, according to one or more embodiments.

FIG. 12 sets forth a flowchart of a computer-implemented process 1200 for tuning a beam spot in a radiation therapy system based on measurements of a radiation field, according to one or more embodiments. In the embodiments, as part of the beam-tuning process, one or more of the above-described radiation field quality metrics are employed to determine whether a beam spot is outside a specified quality range. Computer-implemented process 1200 can be performed as a part of factory setup of a radiation therapy system, as an on-site quality-assurance tool for the radiation therapy system, and/or as a periodic service tool for the radiation therapy system.

Computer-implemented process 1200 may include one or more operations, functions, or actions as illustrated by one or more of blocks 1210-1295. Although the blocks are illustrated in a sequential order, these blocks may be performed in parallel, and/or in a different order than those described herein. Also, the various blocks may be combined into fewer blocks, divided into additional blocks, and/or eliminated based upon the desired implementation. Although computer-implemented process 1200 is described in conjunction with the X-ray imaging system described herein as part of RT system 100 and FIGS. 1-5, persons skilled in the art will understand that any suitably configured X-ray imaging system is within the scope of the present embodiments.

The control algorithms for the blocks of computer-implemented process 1200 may be performed by any suitable computing device or devices. For example, in some embodiments, some or all of the control algorithms for the blocks of computer-implemented process 1200 reside in image acquisition and treatment control computer 109, remote control console 111, a combination of both, or any other computing device communicatively coupled to RT system 100. The control algorithms can be implemented in whole or in part as software- or firmware-implemented logic, and/or as hardware-implemented logic circuits.

In step 1210, a suitable computing device causes optimization of a particular treatment beam to be performed. In some embodiments, such treatment beam optimization in includes confirming a maximum dose rate of treatment beam 230 using conventional techniques known in the art and, when required, performing one or more beam output optimization procedures configure treatment beam 230 to have a suitable maximum dose rate. In some embodiments, step 1210 is substantially similar to step 810 in computer-implemented process 800 of FIG. 8.

In step 1215, one or more procedures are performed to ensure that treatment beam 230 is correctly aligned with respect to collimator rotation axis 308, about which MLC 306 rotates. Additionally, in some embodiments, one or more procedures are performed to ensure that a filter included in collimator assembly 208 is positioned correctly with respect to collimator rotation axis 308. In some embodiments, to complete step 1215, conventional procedures known in the art may be performed.

In step 1220, the computing device causes beam spot 302 of RT system 100 to be measured, for example by the acquisition of a sequence of X-ray projection images of beam spot 302 and the application of an edge measurement algorithm, as described above in conjunction with FIG. 5. In some embodiments, step 1220 is substantially similar to step 820 in computer-implemented process 800 of FIG. 8.

In step 1230, the computing device determines a value for one or more beam spot quality metrics for beam spot 302, based on the output of step 1220. In some embodiments, step 1230 is substantially similar to step 830 in computer-implemented process 800 of FIG. 8.

In step 1240, the computing device determines whether beam spot 302 satisfies a predetermined beam spot quality specification. When the computing device determines that beam spot 302 satisfies the predetermined beam spot quality specification, computer-implemented process 1200 proceeds to step 1260. When the computing device determines that beam spot 302 fails to satisfy the predetermined beam spot quality specification, computer-implemented process 1200 proceeds to step 1250. In some embodiments, step 1240 is substantially similar to step 840 in computer-implemented process 800 of FIG. 8.

In step 1250, the computing device modifies one or more parameters of an electron-beam-shaping component of RT system 100 to a new value. In some embodiments, step 1250 is substantially similar to step 850 in computer-implemented process 800 of FIG. 8.

In step 1260, the computing device causes one or more attributes of a radiation field generated by beam spot 302 to be measured. In some embodiments, in step 1260 one or more slit-field X-ray images of a radiation field of a treatment beam 230 are generated using EPID 105. In such embodiments, multiple slit-field X-ray images of the radiation field may be generated, one slit-field X-ray image for each of multiple evaluation angles. In such embodiments, for each slit-field X-ray image, a rectangular aperture formed by MLC 306 is oriented at a different evaluation angle.

In step 1265, the computing device radiation field analysis is performed. In such embodiments, one or more radiation field quality metrics are determined, such as an area coincidence factor, a penumbra asymmetry factor, and/or an X-ray beam output factor.

In step 1270, the computing device determines whether a radiation field of treatment beam 230 (which was used to generate the multiple slit-field X-ray images) satisfies a predetermined radiation field quality specification. When the computing device determines that the radiation field satisfies the predetermined radiation field quality specification, computer-implemented process 1200 proceeds to step 1295. When the computing device determines that the radiation field fails to satisfy the predetermined radiation field quality specification, computer-implemented process 1200 proceeds to step 1275.

In some embodiments, in step 1270 the computing device determines whether the radiation field satisfies the predetermined radiation field quality specification based on one or more of the radiation field quality metrics determined in step 1265. In some embodiments, in step 1270 the computing device determines whether the radiation field satisfies the predetermined radiation field quality specification based a scoring of multiple radiation field quality metrics. For example, in some embodiments, the radiation field fails to satisfy the predetermined radiation field quality specification when a total score associated with the radiation field does not meet or exceed a specified threshold value for the total score. Alternatively or additionally, in some embodiments, the radiation field fails to satisfy the predetermined radiation field quality specification when a value for at least one of the radiation field quality metrics associated with the radiation field fails to meet a minimum required threshold value or exceeds a maximum allowable threshold value for that radiation field quality metric. In some embodiments, each radiation field quality metric may have a different score weighting, depending on the relative importance of each radiation field quality metric.

Further, in some embodiments, a predetermined radiation field quality specification may include multiple threshold values for one or more radiation field quality metrics. Similar to the above-described beam spot quality metrics, in such embodiments, for a particular radiation field quality metric, the predetermined radiation field quality specification may include one or more upper control limits and one or more lower control limits for beam spot 302. In such embodiments, the upper and lower control limit values can indicate different scoring penalties/rewards.

In step 1275, the computing device modifies one or more parameters of an electron-beam-shaping component of RT system 100 to a new value. As a result, one or more attributes of beam spot 302 are changed that affect 2D intensity distribution 305 of beam spot 302 and, in turn, the radiation field of the treatment beam 230 generated by beam spot 302. In some embodiments, step 1275 is substantially similar to step 1250 described above.

In step 1280, the computing device causes optimization of the particular treatment beam to be performed. In some embodiments, the computing device confirms a maximum dose rate of treatment beam 230 using conventional techniques known in the art and, when required, performs one or more beam output optimization procedures configure treatment beam 230 to have a suitable maximum dose rate. In some embodiments, step 1280 is substantially similar to step 1210 described above.

In step 1285, one or more procedures are performed to ensure that treatment beam 230 is correctly aligned with respect to collimator rotation axis 308, about which MLC 306 rotates. In some embodiments, step 1285 is substantially similar to step 1215 described above.

In step 1290, the computing device causes optimization of the particular treatment beam to be performed. In some embodiments, the computing device confirms a maximum dose rate of treatment beam 230 using conventional techniques known in the art and, when required, performs one or more beam output optimization procedures configure treatment beam 230 to have a suitable maximum dose rate. In some embodiments, step 1290 is substantially similar to step 1210 described above. Upon completion of step 1290, computer-implemented process 1200 returns to step 1220.

In step 1295, computer-implemented process 1200 ends.

In the embodiments described above, the examples of slit-field images depicted are generated using collimator aperture sizes associated with a small-field radiation treatment (e.g., treatments involving radiation fields on the order of a few millimeters). In other embodiments, slit-field images that are generated for measuring the herein-described radiation field quality metrics may be generated using different collimator apertures sizes, such as apertures associated with beam sizes on the order of one or more centimeters.

Figure 13:
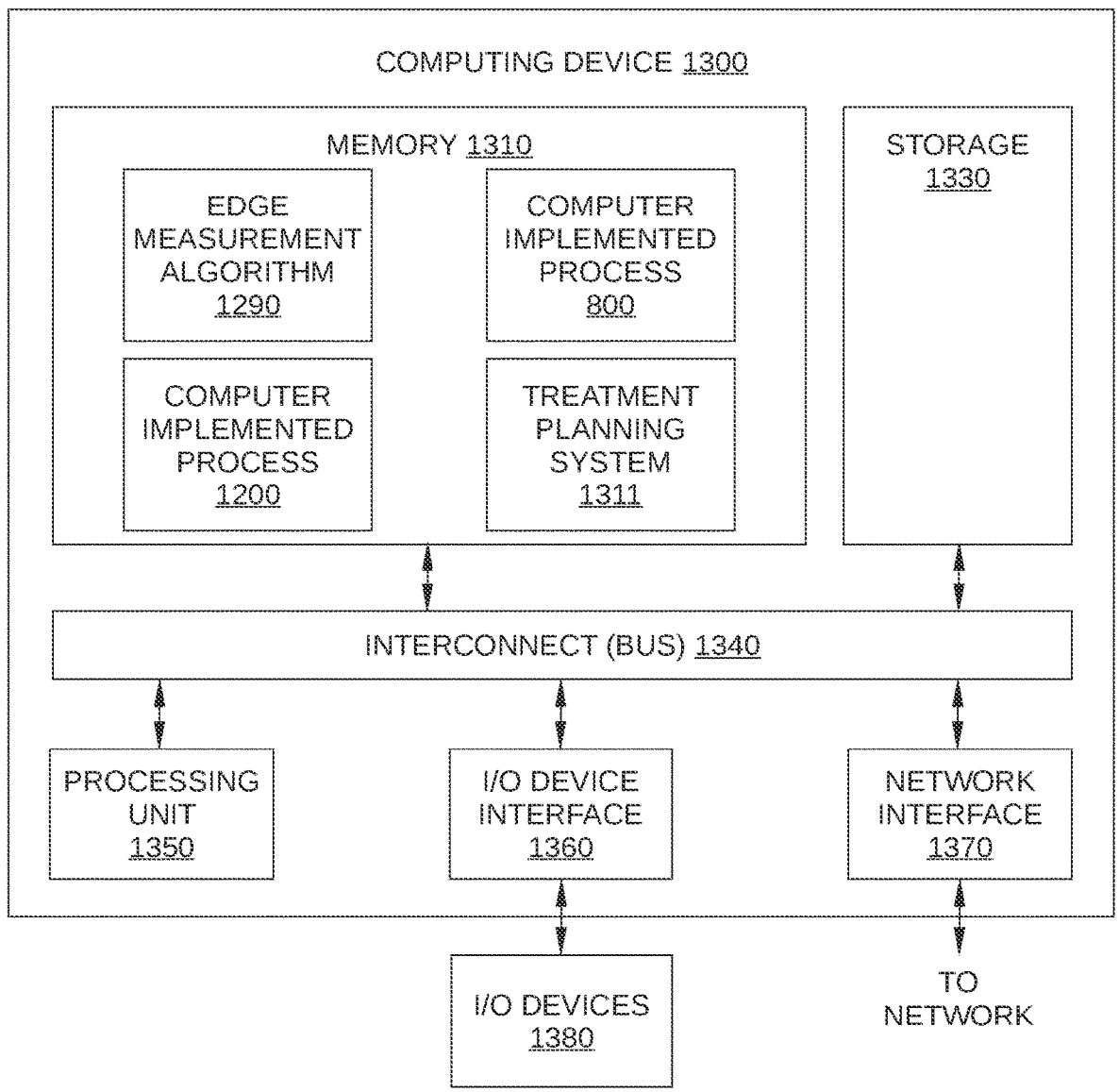
FIG. 13 is an illustration of computing device configured to perform various embodiments of the present disclosure.

FIG. 13 is an illustration of a computing device 1300 configured to perform various embodiments of the present disclosure. Computing device 1300 may be a desktop computer, a laptop computer, a smart phone, or any other type of computing device suitable for practicing one or more embodiments of the present disclosure. In operation, computing device 1300 is configured to execute instructions associated with an edge measurement algorithm 1390, computer-implemented process 800, computer-implemented process 1200, and/or a treatment planning system 1311, as described herein. It is noted that the computing device described herein is illustrative and that any other technically feasible configurations fall within the scope of the present disclosure.

As shown, computing device 1300 includes, without limitation, an interconnect (bus) 1340 that connects a processing unit 1350, an input/output (I/O) device interface 1360 coupled to input/output (I/O) devices 1380, memory 1310, a storage 1330, and a network interface 1370. Processing unit 1350 may be any suitable processor implemented as a central processing unit (CPU), a graphics processing unit (GPU), an application-specific integrated circuit (ASIC), a field programmable gate array (FPGA), any other type of processing unit, or a combination of different processing units, such as a CPU configured to operate in conjunction with a GPU or digital signal processor (DSP). In general, processing unit 1350 may be any technically feasible hardware unit capable of processing data and/or executing software applications, including edge measurement algorithm 1390, computer-implemented process 800, computer-implemented process 1200, and/or treatment planning system 1311.

I/O devices 1380 may include devices capable of providing input, such as a keyboard, a mouse, a touch-sensitive screen, and so forth, as well as devices capable of providing output, such as a display device and the like. Additionally, I/O devices 1380 may include devices capable of both receiving input and providing output, such as a touchscreen, a universal serial bus (USB) port, and so forth. I/O devices 1380 may be configured to receive various types of input from an end-user of computing device 1300, and to also provide various types of output to the end-user of computing device 1300, such as displayed digital images or digital videos. In some embodiments, one or more of I/O devices 1380 are configured to couple computing device 1300 to a network.

Memory 1310 may include a random access memory (RAM) module, a flash memory unit, or any other type of memory unit or combination thereof. Processing unit 1350, I/O device interface 1360, and network interface 1370 are configured to read data from and write data to memory 1310. Memory 1310 includes various software programs that can be executed by processor 1350 and application data associated with said software programs, including edge measurement algorithm 1390, computer-implemented process 800, computer-implemented process 1200, and/or treatment planning system 1311.

Figure 14:
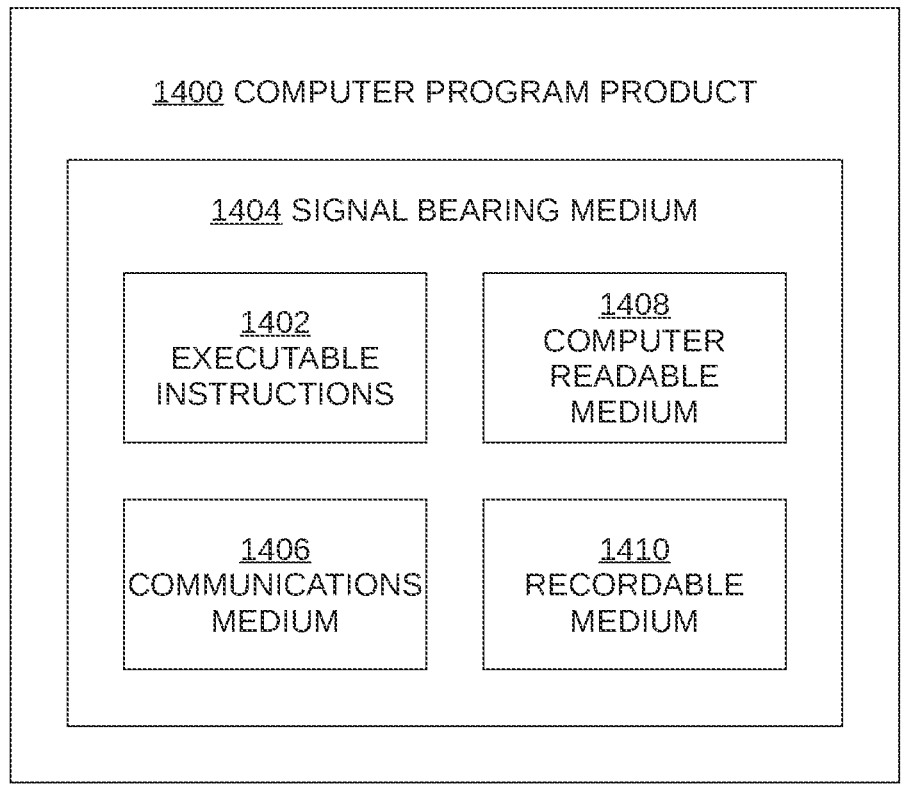
FIG. 14 is a block diagram of an illustrative embodiment of a computer program product for implementing a method for segmenting an image, according to one or more embodiments of the present disclosure.

FIG. 14 is a block diagram of an illustrative embodiment of a computer program product 1400 for implementing a method for segmenting an image, according to one or more embodiments of the present disclosure. Computer program product 1400 may include a signal bearing medium 1404. Signal bearing medium 1404 may include one or more sets of executable instructions 1402 that, when executed by, for example, a processor of a computing device, may provide at least the functionality described above with respect to FIGS. 1-13.

In some implementations, signal bearing medium 1404 may encompass a non-transitory computer readable medium 1408, such as, but not limited to, a hard disk drive, a Compact Disc (CD), a Digital Video Disk (DVD), a digital tape, memory, etc. In some implementations, signal bearing medium 1404 may encompass a recordable medium 1410, such as, but not limited to, memory, read/write (R/W) CDs, R/W DVDs, etc. In some implementations, signal bearing medium 1404 may encompass a communications medium 1406, such as, but not limited to, a digital and/or an analog communication medium (e.g., a fiber optic cable, a waveguide, a wired communications link, a wireless communication link, etc.). Computer program product 1400 may be recorded on non-transitory computer readable medium 1408 or another similar recordable medium 1410.

In sum, embodiments described herein provide techniques for controlling the size, shape, and/or power intensity distribution of a beam spot in a radiation therapy system. The herein-described techniques facilitate tuning of the beam spot to improve consistency between the attributes of the beam spot and pre-configured beam data that is included in a treatment planning model. As a result, performance of an X-ray beam generated by the beam spot closely matches the performance assumed for the X-ray beam in the treatment planning system.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments.

Aspects of the present embodiments may be embodied as a system, method or computer program product. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

We claim:

1. A computer-implemented method for tuning a beam spot in a radiation therapy system, the method comprising:
configuring an electron beam to generate a first beam spot on an electron-beam target of the radiation therapy system;

generating, using an imager of the radiation therapy system, a first plurality of projection images of the first beam spot, wherein each of the projection images of the first beam spot is generated with a line of sight blocked between the imager and a different respective portion of the beam spot by a portion of a collimator of the radiation therapy system;

based on the first plurality of projection images, determining a value for one or more beam spot quality metrics associated with the first beam spot; and based on the value, determining whether the first beam spot is outside a specified quality range.

2. The computer-implemented method of claim 1, further comprising, in response to determining that the first beam spot is outside the specified quality range, modifying at least one parameter of an electron-beam-generating component of the system to a new value.

3. The computer-implemented method of claim 2, wherein modifying the parameter of the electron-beam-shaping component of the system comprises changing a magnitude of a first solenoid current to the new value.

4. The computer-implemented method of claim 1, further comprising, while the imager generates the first plurality of projection images of the first beam spot, for each respective projection image, positioning the portion of the collimator at a different respective rotational angle about a rotation axis of the collimator.

5. The computer-implemented method of claim 1, wherein shaping the first X-ray beam that originates from the first beam spot using the portion of the collimator comprises parking the portion of the collimator in a fixed position relative to a rotation axis of the collimator.

6. The computer-implemented method of claim 1, wherein the one or more beam spot quality metrics include one or more of a beam spot area, a beam spot elongation, a beam spot power per unit area, or a beam spot center point offset from an ideal center point location.

7. The computer-implemented method of claim 1, further comprising, measuring a dose rate of an X-ray beam that originates from the first beam spot.

8. The computer-implemented method of claim 1, wherein determining the value for one or more beam spot quality metrics associated with the first beam spot comprises generating a two-dimensional intensity distribution of the first beam spot.

9. A radiation therapy system, the system comprising:
an imager;
a treatment-delivering radiation source that includes an electron-beam target and is configured to direct a treatment beam to a target volume of patient anatomy; and
one or more processors configured to:
configure an electron beam to generate a first beam spot on the electron-beam target;
generate, using the imager, a first plurality of projection images of the first beam spot, wherein each of the projection images of the first beam spot is generated with a line of sight blocked between the imager and a different respective portion of the beam spot by a portion of a collimator of the radiation therapy system;
based on the first plurality of projection images, determine a value for one or more beam spot quality metrics associated with the first beam spot; and
based on the value, determine whether the first beam spot is outside a specified quality range.

10. The computer-implemented method of claim 9, wherein generating the two-dimensional intensity distribution of the first beam spot comprises reconstructing the two-dimensional intensity distribution using an edge measurement algorithm.

11. The system of claim 9, wherein the one or more processors are further configured to, in response to determining that the first beam spot is outside the specified quality range, modify at least one parameter of an electron-beam-generating component of the system to a new value.

12. The system of claim 11, wherein the one or more processors are further configured to, after modifying the at least one parameter of the electron-beam-shaping component of the system to the new value:
configure the electron beam to generate a second beam spot on the electron-beam target of the radiation therapy system with the electron beam using the new value of the parameter;
generate, using the imager, a second plurality of projection images of the second beam spot, wherein each of the projection images of the second beam spot is generated with a line of sight blocked between the imager and a different respective portion of the beam spot; and
based on the second plurality of projection images, determine a value for the one or more beam spot quality metrics associated with the second beam spot.

13. The system of claim 11, wherein modifying the parameter of the electron-beam-shaping component of the system comprises changing a magnitude of a first solenoid current to the new value.

14. The system of claim 13, wherein modifying the parameter of the electron-beam-shaping component of the system further comprises changing a magnitude of a second solenoid current.

15. The system of claim 9, wherein the one or more processors are further configured to shape a first X-ray beam that originates from the first beam spot using a portion of a collimator of the radiation therapy system while the image generates the first plurality of projection images.

16. The system of claim 15, wherein the one or more processors are further configured to, while the imager generates the first plurality of projection images of the first beam spot, for each respective projection image, position the portion of the collimator at a different respective rotational angle about a rotation axis of the collimator.

17. The system of claim 9, wherein the one or more processors are further configured to, in response to determining that the first beam spot is within the specified quality range:
configure the electron beam to generate the first beam spot on the electron-beam target of the radiation therapy system;
determine a value for one or more radiation field quality metrics for a first X-ray beam that originates from the first beam spot; and
based on the value for the one or more radiation field quality metrics, determining whether the first X-ray beam is outside a specified radiation field quality range.

18. The system of claim 9, wherein modifying the parameter of the electron-beam-shaping component of the system comprises changing a directionality of a first solenoid current.

19. The system of claim 18, wherein modifying the parameter of the electron-beam-shaping component of the system further comprises changing a directionality of a second solenoid current.

20. A method of improving consistency between one or more attributes of a beam spot in a radiation therapy system and pre-configured beam data included in a treatment planning model of the radiation therapy system, the method comprising:
- measuring the one or more attributes of a first beam spot based on a plurality of projection images of the first beam spot, wherein each of the projection images of the first beam spot is generated with a line of sight blocked between an imager of the radiation therapy system and a different respective portion of the beam spot by a portion of a collimator of the radiation therapy system;
- determining a value for one or more radiation field quality metrics for a radiation beam that originates from the first beam spot;
- based on at least one of the one or more attributes of the first beam spot and the value for the one or more radiation field quality metrics for the radiation beam, modifying a parameter of an electron-beam-generating component of the radiation therapy system from a first value to a second value; and
- generating a second beam spot with the electron-beam-generating component of the radiation therapy system using the second value, wherein one or more attributes of the second beam spot are closer in value to the pre-configured beam data than the one or more attributes of the first beam spot.

* * * * *